US012758179B2

(12) United States Patent
Dykowski et al.

(10) Patent No.: US 12,758,179 B2
(45) Date of Patent: Oct. 13, 2026

(54) SYSTEMS AND METHODS FOR AUTOMATED PHANTOM CENTERING

(71) Applicant: GE Precision Healthcare LLC, Waukesha, WI (US)

(72) Inventors: Maxwell James Dykowski, Waukesha, WI (US); Daniel Joseph Grieshop, Wauwatosa, WI (US); John M Boudry, Waukesha, WI (US); Chelsey Amanda Lewis, Waukesha, WI (US); Changlyong Kim, Brookfield, WI (US); Tyler Curtis, Wauwatosa, WI (US); Jean-Baptiste Thibault, Waukesha, WI (US); Olof Hugo Mauritz Linder, Stockholm (SE)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 138 days.

(21) Appl. No.: 18/783,191

(22) Filed: Jul. 24, 2024

(65) Prior Publication Data

US 2026/0026768 A1 Jan. 29, 2026

(51) Int. Cl.

*A61B 6/58* (2024.01)
*A61B 6/03* (2006.01)
*A61B 6/04* (2006.01)

(52) U.S. Cl.

CPC ................ *A61B 6/585* (2013.01); *A61B 6/03* (2013.01); *A61B 6/0407* (2013.01); *A61B 6/0492* (2013.01)

(58) Field of Classification Search

CPC ......... A61B 6/585; A61B 6/03; A61B 6/0407; A61B 6/0492; A61B 6/0487; A61B 6/545; A61B 6/583

See application file for complete search history.

(56) References Cited

U.S. PATENT DOCUMENTS 5,214,578 A 5/1993 Cornuejols et al.
8,411,814 B2 4/2013 Naidu et al.
11,400,317 B2 8/2022 Yang (Continued)

FOREIGN PATENT DOCUMENTS

DE 202015001484 U1 5/2016
EP 3630284 B1 4/2023

(Continued)

OTHER PUBLICATIONS

Daniel E Hyer et al: “Development and implementation of an EPID-based method for localizing isocenter”, Journal of applied clinical medical physics / American College of Medical Physics, Jan. 1, 2012 (Jan. 1, 2012), p. 3965, XP055168550, United States DOI: 10.1120/jacmp.v13i6.3965 Retrieved from the Internet: URL:http://www.ncbi.nlm.nih.gov/pubmed/231 49787 A * p. 77, 2nd and third paragraph; p. 76, 19, lines from top *.

(Continued)

*Primary Examiner* — Kiho Kim
(74) *Attorney, Agent, or Firm* — McCoy Russell LLP

(57) ABSTRACT

Systems and methods are herein provided for automatic phantom centering. In one example, a method for an imaging system comprises acquiring scan data of a phantom; determining one or more distances to center of the phantom; and automatically adjusting a position of the phantom based on the one or more distances to center.

20 Claims, 13 Drawing Sheets

(56) References Cited

U.S. PATENT DOCUMENTS

| | | | | |
|---|---|---|---|---|
| 2012/0076371 | A1* | 3/2012 | Caruba | A61B 6/4417 250/252.1 |
| 2012/0093282 | A1 | 4/2012 | Kappler | |
| 2018/0133508 | A1 | 5/2018 | Pearce et al. | |
| 2020/0261050 | A1 | 8/2020 | Bornefalk | |

FOREIGN PATENT DOCUMENTS

| | | | | |
|---|---|---|---|---|
| JP | 2010004959 | A | 1/2010 | |
| JP | 2022502210 | A | 1/2022 | |
| WO | WO-2021203602 | A1 * | 10/2021 | A61B 6/035 |

OTHER PUBLICATIONS

DE202015001484 English Abstract, Machine Translation—Espacenet.com, Mar. 19, 2026; 2 pages.
EP application 25187976.3 filed Jul. 7, 2025—extended Search Report issued Dec. 19, 2025; 8 pages.
JP2010004959 English Abstract, European Patent Office, 1 page.
JP2022502210 English Abstract, Machine Translation—Espacenet.com, Mar. 19, 2026; 2 pages.

* cited by examiner

SYSTEMS AND METHODS FOR AUTOMATED PHANTOM CENTERING

FIELD

Embodiments of the subject matter disclosed herein relate to medical imaging, and more particularly to automated phantom centering.

BACKGROUND

In computed tomography (CT imaging systems, an electron beam generated by a cathode is directed towards a target within an x-ray tube. A fan-shaped or cone-shaped beam of x-rays produced by electrons colliding with the target is directed toward a subject, such as a patient. After being attenuated by the object, the x-rays impinge upon an array of radiation detector elements. An electrical signal is generated at each detector element, and the electrical signals generated at the detector elements are used to reconstruct an image of the object, where each electrical signal corresponds to a voxel/pixel of the image.

A quality of the image in terms of resolution, contrast-to-noise ratio, and other factors may depend on an alignment of each detector element within the detector arrays. Misalignments of the detector elements may increase a number of artifacts in the image and/or reduce the quality of the image. A calibration process may be performed periodically on the system to obtain projection data of materials that simulate varying human tissue densities. The calibration process may include performing an x-ray scanning procedure on an object, called a phantom. Physical misalignment of a phantom during a calibration process may result in inaccurate calibration of the CT system.

BRIEF DESCRIPTION

In one example, a method for an imaging system, comprises: acquiring scan data of a phantom; determining one or more distances to center of the phantom; and automatically adjusting a position of the phantom based on the one or more distances to center.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
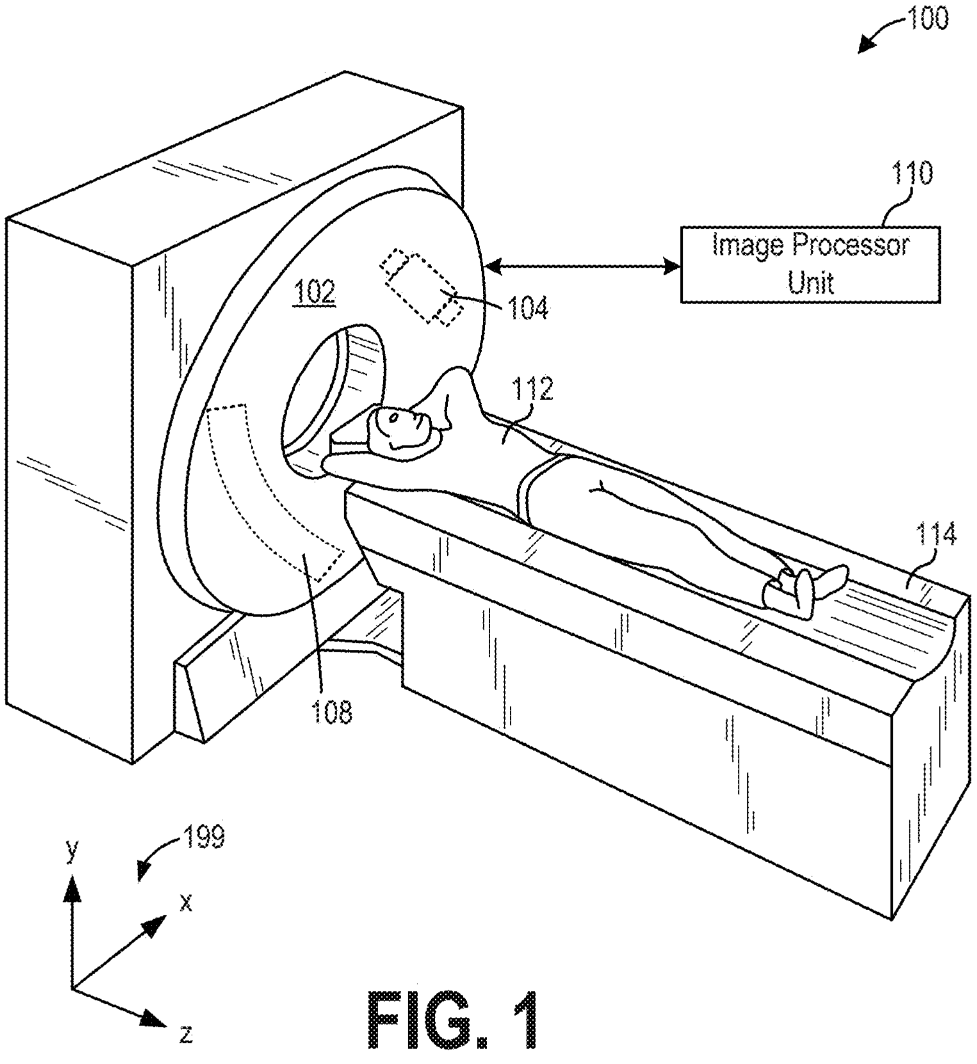
FIG. 1 shows a pictorial view of an imaging system, according to an embodiment.

The description and embodiments of the subject matter disclosed herein relate to automated phantom centering for calibration scans of an imaging system, such as a computed tomography (CT system). Some imaging systems, such as CT systems or photon counting computing tomography (PCCT) systems, may demand relatively regular calibration, such as daily or weekly calibration scans to offset any gain drive, for example realized from hardware such as x-ray tube focal spot position change or radiation degradation of the detectors. Further, PCCT or CT systems may obtain spectral information that allows generation of basis material decomposition (BMD) images. Calibrating PCCT systems may thereby demand that calibration projection data be obtained that mimics the materials and material thicknesses of the human body. Thus, phantoms for calibrating PCCT systems may include multiple different materials, such as polyvinyl chloride (PVC) and polyethylene (PE). Phantoms of multiple types are available for calibration purposes, including slab phantoms, step phantoms, pillar phantoms, and more.

Accurate calibration using phantoms is dependent upon proper alignment of the phantom. Currently, phantoms, placed in an accessory slot or upon a table of the imaging system, are aligned in a predetermined position, for example at an isocenter of the imaging system, manually. For example, a user (e.g., a technician) manually aligns the phantom with the isocenter via manual gantry controls with aid of laser guides and scout scans. However, this manual process is prone to misalignment errors and can often take up unnecessary time in repeated realigning of the phantom and/or repeating phantom imaging when images are acquired with misaligned phantoms.

Systems and methods are thus herein provided for automated phantom centering that at least partially address the above mentioned issues. For example, one or more distances to an isocenter of the imaging system may be determined in order to determine an amount of misalignment and thus movements needed to center the phantom. Based on the one or more distances, the imaging system may automatically move the phantom (e.g., move the table on which the phantom or a holder for the phantom is placed) to center it.

In some examples, an edge finding algorithm may be applied to determine one or more of the distances. For example, the edge finding algorithm may be applied to determine the distance in the z-direction and/or the x-direction. Further, in some examples, an amount of tilt misalignment may be determined based on pixel counts within scan data acquired of the phantom. Differences between pixel counts for left and right-most pixels may indicate the amount of tilt misalignment. In this way, the phantom may be automatically centered laterally, longitudinally, vertically, and rotationally based on computed distances and tilts. Without inclusion of human error in manually aligning the phantom, the accuracy of calibration may be increased. Further, time may be saved for the user by reducing need for repeated manual placements and/or repeated acquisitions.

FIG. 1 illustrates an exemplary imaging system. The imaging system as shown may be a CT system, and in particular a PCCT system 100 (also referred to as a photon counting X-ray imaging system) configured for CT imaging with photon counting detectors, though it should be understood that other imaging systems, such as conventional CT, magnetic resonance imaging (MRI), positron emission tomography (PET) systems, and more may be used without departing from the scope of this disclosure. An axis system 199 is provided in FIG. 1 (and FIGS. 9A-10B). An x-axis of the axis system 199 may be a lateral axis (e.g., a left-right axis), a y-axis may be a vertical axis (e.g., parallel with a gravitational axis), and a z-axis may be a longitudinal axis (e.g., an axis in/out of the gantry).

Particularly, the PCCT system 100 is configured to image a subject 112 such as a patient, an inanimate object, one or more manufactured parts, and/or foreign objects such as dental implants, stents, and/or contrast agents present within the body. The PCCT system 100 includes a gantry 102, which in turn, may further include at least one X-ray source 104 configured to project a beam of X-ray radiation 106 (see FIG. 2) for use in imaging the subject 112 laying on a table 114. Specifically, the X-ray source 104 is configured to project the X-ray radiation beams 106 towards a detector array 108 positioned on the opposite side of the gantry 102. Although FIG. 1 depicts a single X-ray source 104, in certain embodiments, multiple X-ray sources and detectors may be employed to project a plurality of X-ray radiation beams for acquiring projection data at the same or different energy levels corresponding to the patient. In the embodiments described herein, the X-ray detector employed is a photon counting detector which is capable of differentiating X-ray photons of different energies.

In certain embodiments, the PCCT system 100 further includes an image processor unit 110 configured to reconstruct images of a target volume of the subject 112 using an iterative or analytic image reconstruction method. For example, the image processor unit 110 may use an analytic image reconstruction approach such as filtered back projection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. In some examples the image processor unit 110 may use an analytic image reconstruction approach such as FBP in addition to an iterative image reconstruction approach.

In some CT imaging system configurations, an X-ray source projects a cone-shaped X-ray radiation beam which is defined with respect to an X-Y-Z Cartesian coordinate system and generally referred to as an "imaging volume." The X-ray radiation beam passes through an object being imaged, such as the patient or subject. The X-ray radiation beam, after being attenuated by the object, impinges upon an array of detector elements. The intensity of the attenuated X-ray radiation beam received at the detector array is dependent upon the attenuation of an X-ray radiation beam by the object. Each detector element of the array produces a separate electrical signal that is a measurement of the X-ray beam attenuation at the detector location. The attenuation measurements from all the detector elements are acquired separately to produce a transmission profile.

In some CT systems, the X-ray source and the detector array are rotated with a gantry within the imaging volume and around the object to be imaged such that an angle at which the X-ray beam intersects the object constantly changes. A group of X-ray radiation attenuation measurements, e.g., projection data, from the detector array at one gantry angle is referred to as a "view." A "scan" of the object includes a set of views made at different gantry angles, or view angles, during one revolution of the X-ray source and detector.

Figure 2:
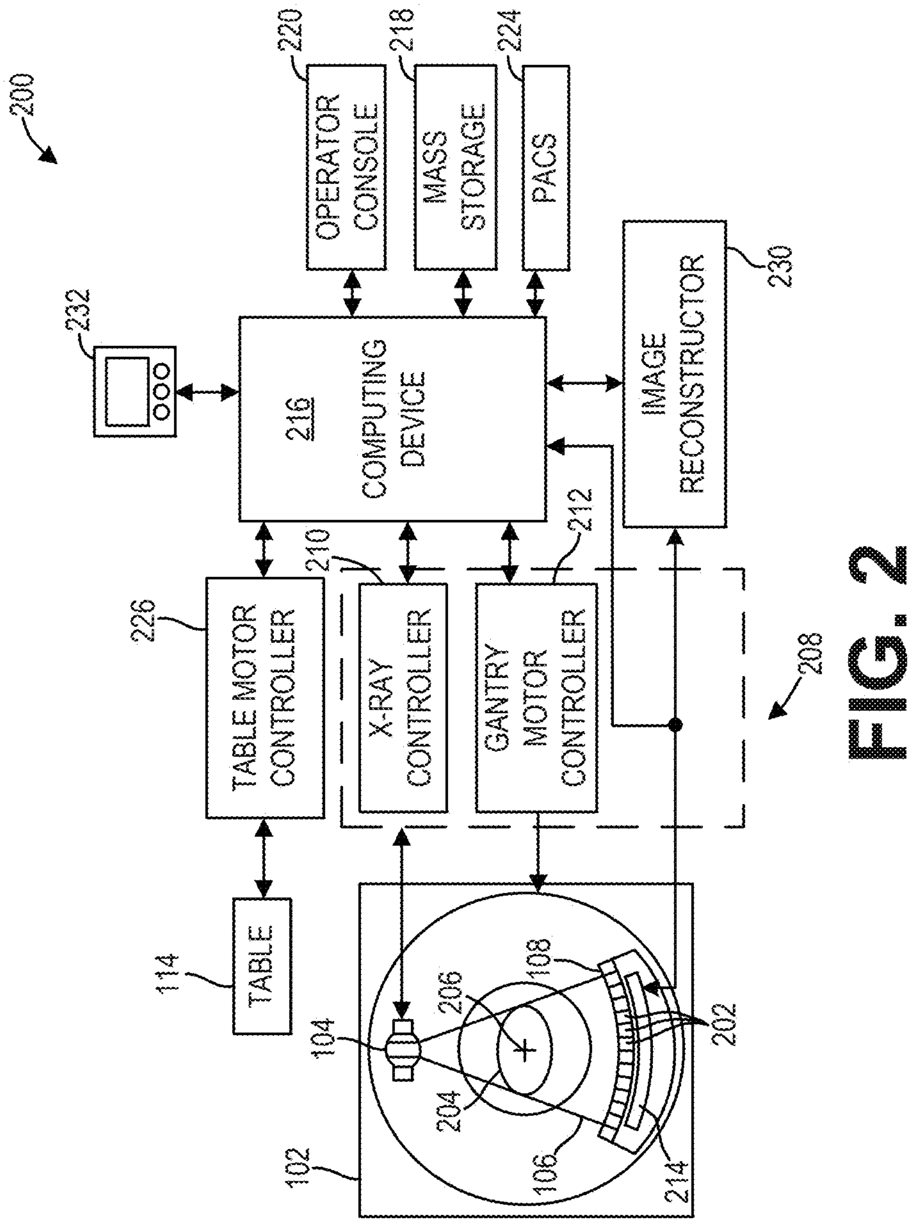
FIG. 2 shows a block schematic diagram of an exemplary imaging system, according to an embodiment.

FIG. 2 illustrates an exemplary imaging system 200 similar to the PCCT system 100 of FIG. 1. In accordance with aspects of the present disclosure, the imaging system 200 is configured for imaging a subject 204 (e.g., the subject 112 of FIG. 1). During certain scans, the subject may be a phantom. A phantom may be an object configured to be scanned by the PCCT system as part of a calibration process for the PCCT system. In one embodiment, the imaging system 200 includes the detector array 108 (see FIG. 1). The detector array 108 further includes a plurality of detector elements 202 that together sense the X-ray radiation beam 106 (see FIG. 2) that passes through the subject 204 (such as a patient) to acquire corresponding projection data. In some embodiments, the detector array 108 may be fabricated in a multi-slice configuration including the plurality of rows of cells or detector elements 202, where one or more additional rows of the detector elements 202 are arranged in a parallel configuration for acquiring the projection data. The detector elements 202 may also be referred to as pixels or detector pixels.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where the projection angle relative to the subject 204 varies as a function of time, the mounted components may be configured to move along a general curve rather than along a segment of a circle.

As the X-ray source 104 and the detector array 108 rotate, the detector array 108 collects data of the attenuated X-ray beams. The data collected by the detector array 108 undergoes pre-processing and calibration to condition the data to represent the line integrals of the attenuation coefficients of the scanned subject 204. The processed data are commonly called projections. In some examples, the individual detectors or detector elements 202 of the detector array 108 may include photon counting detectors which register the interactions of individual photons into one or more energy bins.

The acquired sets of projection data may be used for BMD. During BMD, the measured projections are converted to a set of material-density projections. The material-density projections may be reconstructed to form a set of material-density maps or images of each respective basis material, such as bone, soft tissue, and/or contrast agent maps. The density maps or images may be, in turn, associated to form a 3D volumetric image of the basis material, for example, bone, soft tissue, and/or contrast agent, in the imaged volume.

Once reconstructed, the basis material image produced by the imaging system 200 reveals internal features of the subject 204, expressed in the densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the X-ray source 104. In certain embodiments, the control mechanism 208 further includes an X-ray controller 210 configured to provide power and timing signals to the X-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate data from a subset of the detector elements 202 into so-called macro-detectors. The data sampled and digitized by the DAS 214 is transmitted to a computer or computing device 216. In one example, the computing device 216 stores the data in a storage device or mass storage 218. The storage device 218, for example, may be any type of non-transitory memory and may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the X-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the target volume of the subject 204. In particular, the computing device 216 may be configured to control movement of the table 114 in one or more directions. For example, in some examples, the computing device 216 may be configured to control movement of the gantry 102 in a y-direction and a z-direction but not in an x-direction, wherein the directions correspond to the axis system 199 provided in FIG. 1. In other embodiments, the computing device 216 may be configured to control movement of the table 114 in all of the x-direction, y-direction, and z-direction. Further, the computing device 216 may be configured to control tilt of the table 114, for example via rotation of the table about the z-axis and/or x-axis.

As previously noted, the DAS 214 samples and digitizes the projection data acquired by the detector elements 202. Subsequently, an image reconstructor 230 uses the sampled and digitized X-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 may transmit the reconstructed images to the computing device 216 to generate useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

Information may be transmitted between the components residing in the gantry 102 and external devices (such as the computing device 216 and/or image reconstructor 230), which facilitates electronic communication across the rotating gantry. In some examples, the gantry and internal components (e.g., the control mechanism 208, X-ray source 104, the detector array 108) may be collectively defined as a PCCT scanner, and as such the computing device 216 and image reconstructor 230 may reside off the scanner.

The various methods and processes (such as the method described below with reference to FIGS. 3-8) described further herein may be stored as executable instructions in non-transitory memory on a computing device (or controller) in imaging system 200. In one embodiment, the computing device 216 and/or the image reconstructor 230 may include such executable instructions in non-transitory memory, and may apply the methods described herein to reconstruct an image and compute distances for centering the phantom. In another embodiment, computing device 216 may include the instructions in non-transitory memory, and may apply the methods described herein, at least in part, to a reconstructed image after receiving the reconstructed image from image reconstructor 230. In yet another embodiment, the methods and processes described herein may be distributed across image reconstructor 230 and computing device 216.

In one embodiment, the display 232 allows the operator to evaluate the imaged anatomy. The display 232 may also allow the operator to select a volume of interest (VOI) and/or request patient information, for example, via a graphical user interface (GUI) for a subsequent scan or processing.

It should be appreciated that while a PCCT system is herein described, other imaging systems may be utilized without departing from the scope of this disclosure, including conventional CT systems, MRI systems, PET systems, single photon emission computerized tomography (SPECT) systems, and the like.

Figure 3:
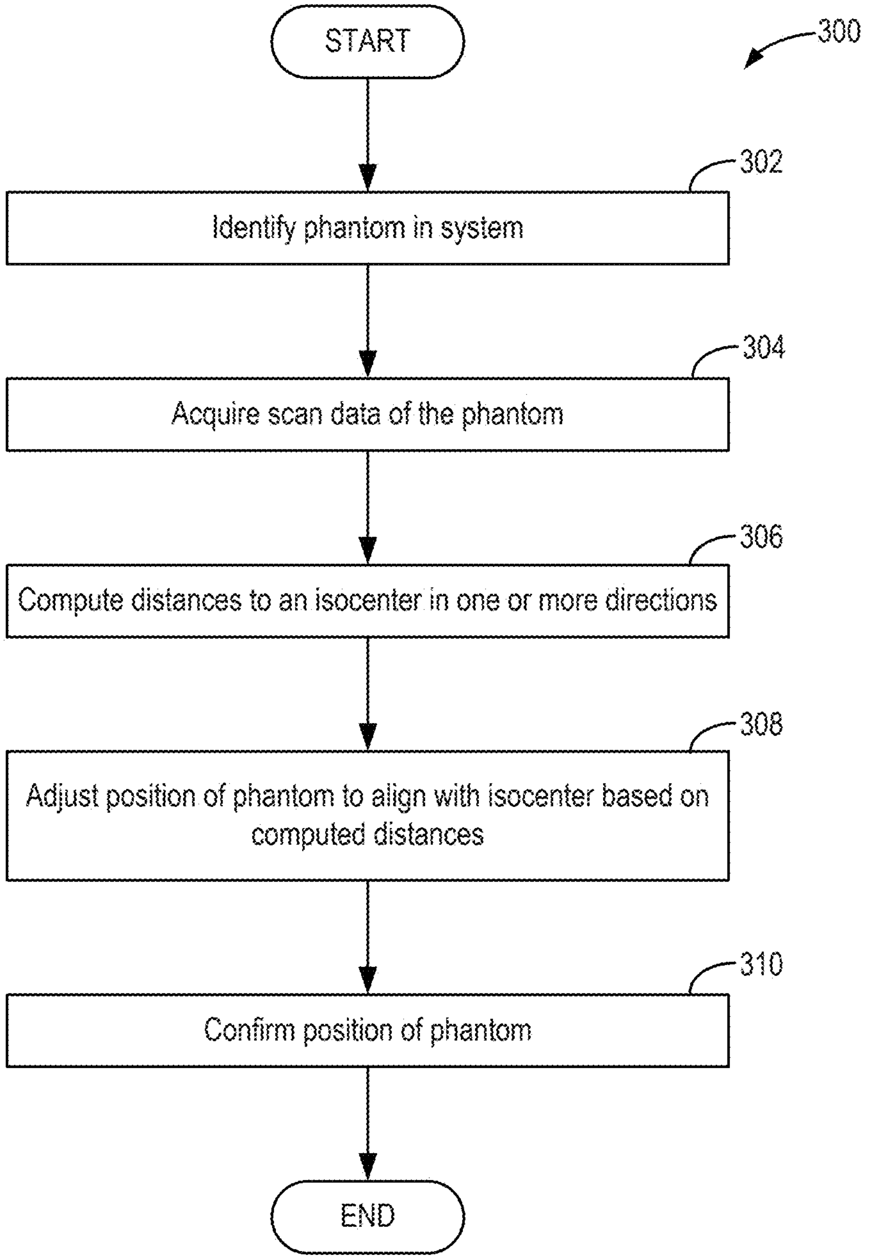
FIG. 3 shows a flowchart illustrating a high-level method for automated phantom centering.

Turning now to FIG. 3, a flowchart illustrating a high-level method 300 for automated phantom centering, according to a first embodiment. At least some aspects of the method 300 may be carried out according to instructions stored in memory and executed by one or more processors of an imaging system, such as computing device 216 of imaging system 200. In some examples, one or more aspects of the method 300 may be carried out manually by a user. In some examples, the method 300 may be performed in real-time.

At 302, method 300 includes identifying a phantom in the imaging system. As described above, phantoms may be placed in an accessory slot or upon a table of the imaging system (e.g., in a designated holder) by the user in an initial position. The phantom may be placed at approximately an isocenter of the imaging system. In some examples, laser guides may be present to guide the user to the isocenter and the user may manually operate gantry controls for approximate centering. The phantom may be one of a plurality of identifiable phantoms known to the system. In some examples, the phantom may be identified by one or more parameters of a scout scan acquired of the phantom in the initial position. In other examples, the phantom may be identified based on user inputs. For example, the user may indicate, via selection of an option in a drop down menu, via a search query, or the like, the type of phantom present. In yet further examples, the phantom may be identified using radiofrequency identification (RFID) confirmation via RFID tags or with a patient positioning camera.

At 304, method 300 includes acquiring scan data of the phantom. The scan data of the phantom may be a scout scan or axial scan, in some examples, acquired with a lower resolution than a conventional scan. In some examples, the scan data may be acquired following confirmation from the computing device that an elevation of a table of the system (e.g., placement in the y-direction) is sufficient for scanning. If not, the computing device may instruct the control mechanism for the gantry to move the table in the y-direction into a sufficient elevation. If the elevation of the table is changed, the initial position of the phantom may be updated based on the new elevation.

Figure 4:
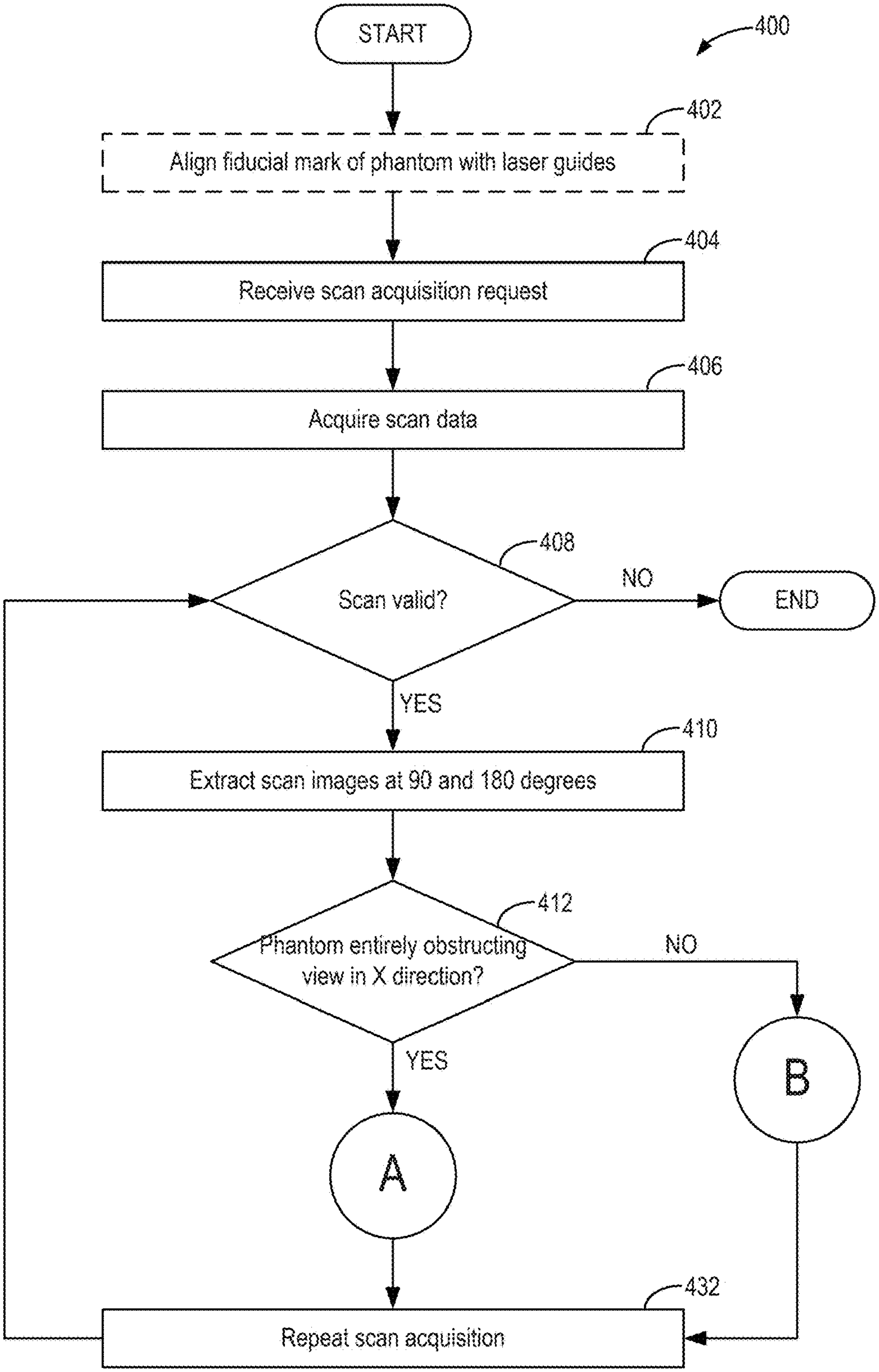
FIG. 4 shows a flowchart illustrating a method for determining centering distances for an imaging system according to a first embodiment.
Figure 5:
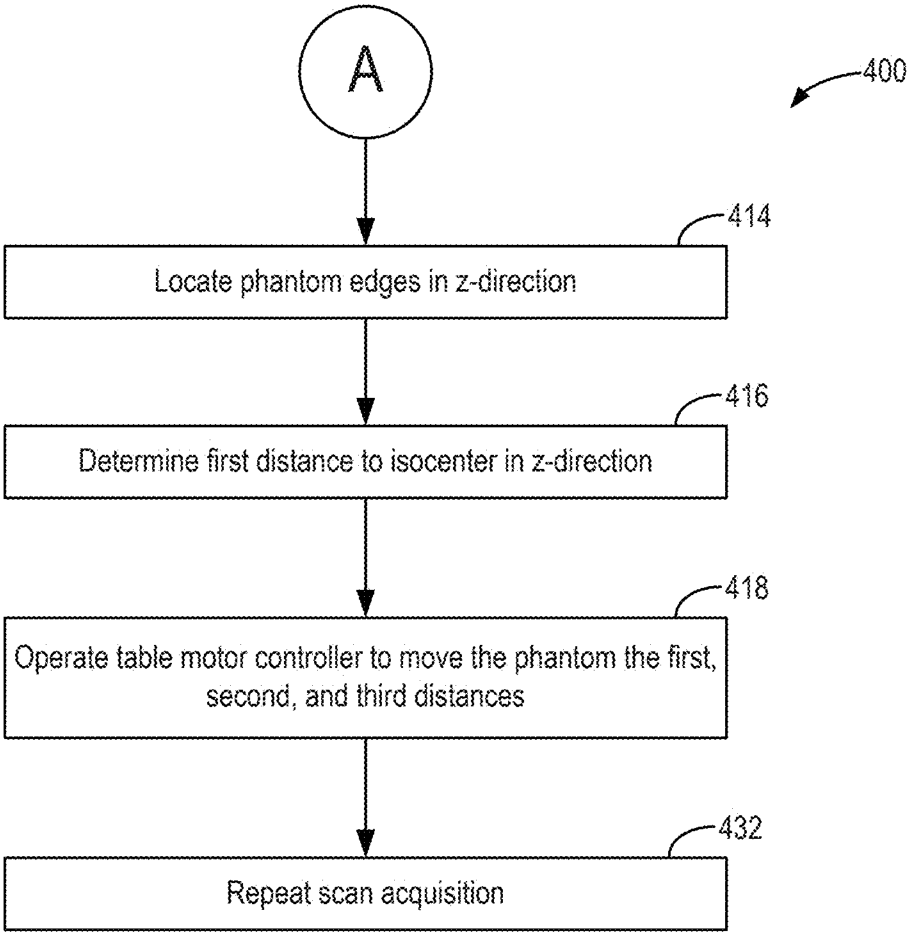
FIG. 5 continues the flowchart of FIG. 4.
Figure 6:
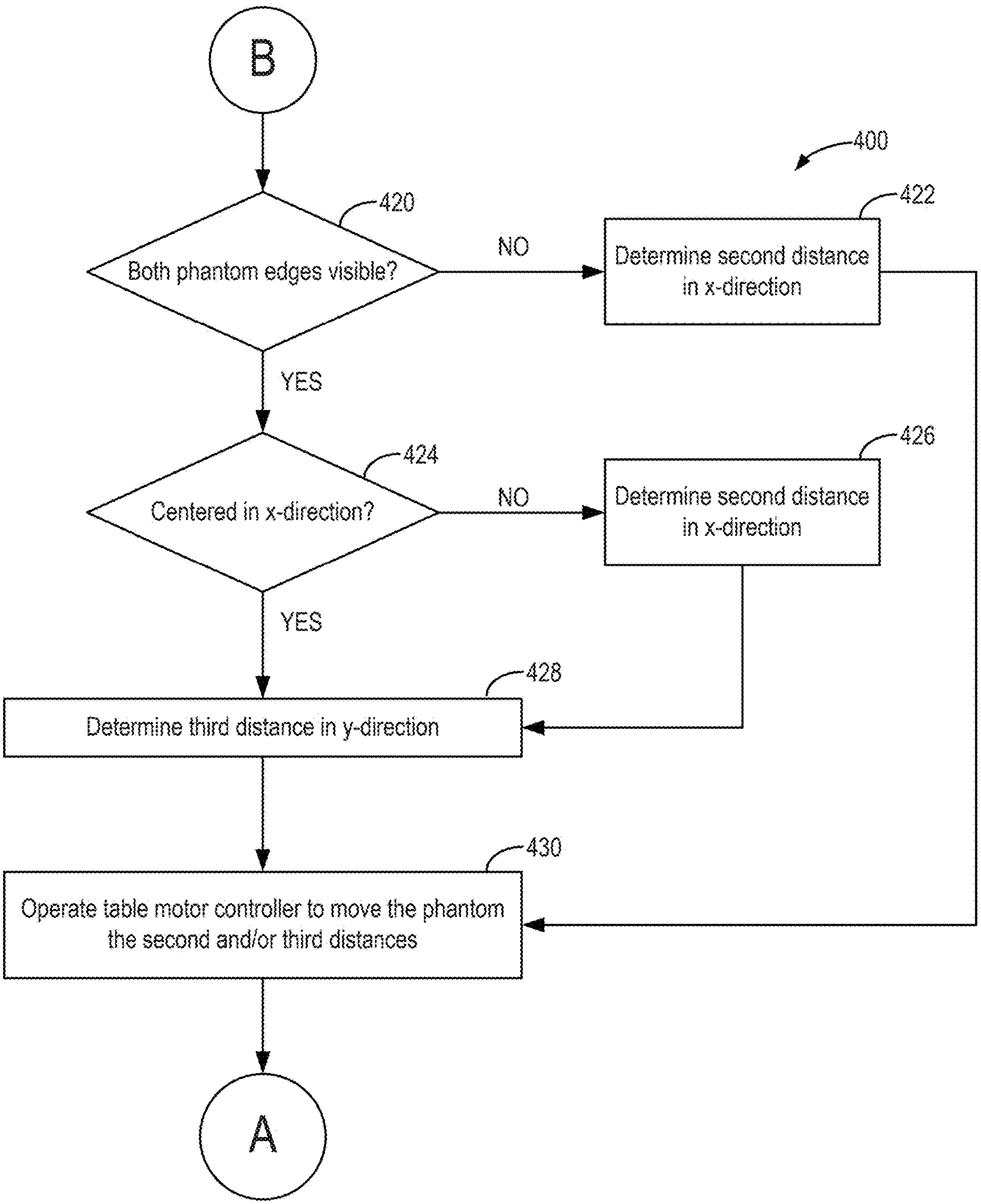
FIG. 6 continues the flowchart of FIG. 4.
Figure 7:
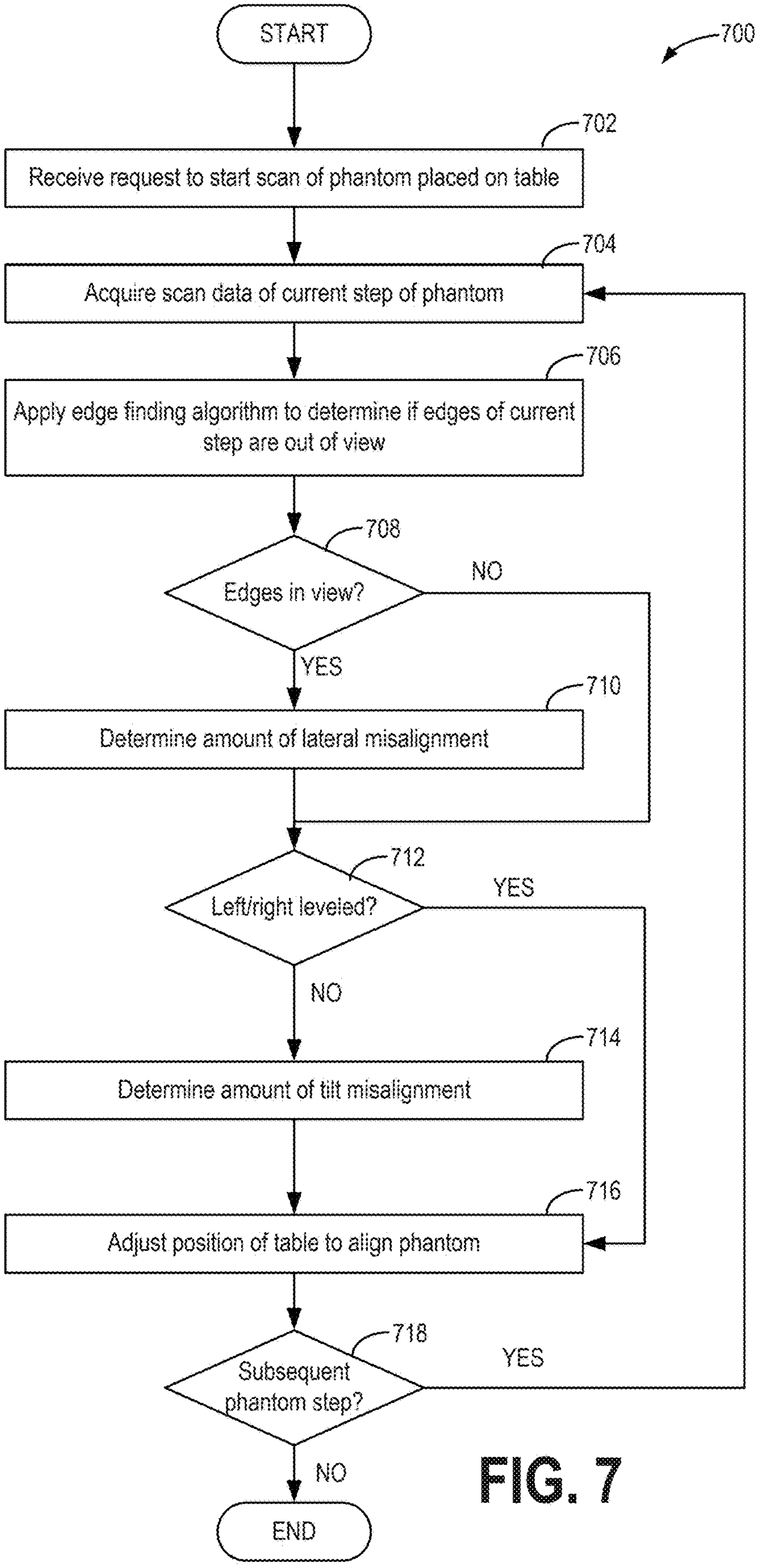
FIG. 7 shows a flowchart illustrating a method for automated phantom centering according to a second embodiment.

At 306, method 300 includes computing distances to an isocenter in one or more directions. As will be further described with respect to FIGS. 4-7, the distances may be computed in the x-direction, the y-direction, and/or the z-direction. In some instances, automated movement in the x-direction may not be available. However, a distance to the isocenter in the x-direction in such cases may still be determined. In particular, FIGS. 4-7 present various embodiments for methods of determining the distances to the isocenter. Namely, FIGS. 4-6 show methods for computing distances based on determining positions of the edges with respect to the isocenter in lateral and vertical directions while FIG. 7 shows a method for automatically centering step/slab phantoms in lateral directions and rotationally.

At 308, method 300 includes adjusting a position of the phantom to align with the isocenter based on the computed distances. As an example, the position of the phantom may be adjusted in the z-direction based on a first computed distance in the z-direction, whereby a position of the table within the gantry in the z-direction is adjusted the first computed distance. In some examples, all gantry-controlled table movements may be automated and thus executed automatically in response to determination of the computed distances, including all of lateral translation (e.g., movement in the x-direction), longitudinal translation (e.g., movement in the z-direction), change in elevation (e.g., movement of the table in the y-direction), and table tilt (e.g., rotation of the table about the z-axis). In other examples, movements of the table may be executed automatically for one or more but not all of the computed distances. For example, table movement in the x-direction may not be automated, in which case the automated movement may occur for the other directions based on corresponding computed distances, while the user may manually adjust position of the table in the x-direction based on a corresponding distance in the x-direction that is determined at 306.

In addition, the computed distances may be outputted to a display screen of the imaging system. In examples in which automatic table movement in one or more directions is not available, the computed distance in those directions may be presented on the display screen for the user to reference when manually adjusting the table position.

At 310, method 300 includes confirming the position of the phantom. In some examples, confirming the position of the phantom may comprise repeating acquisition of scan data and repeating computation of distances to the isocenter. If the computed distances are within a predefined threshold (e.g., less than 1 mm from the isocenter in all computed directions), the position of the phantom may be confirmed. If misalignment of the phantom is still present, the system may repeat the position adjustments as described above to align the phantom at the isocenter. In this way, the method 300 may be repeated multiple times in order to accurately align the phantom, thereby avoiding misalignment errors in phantom imaging.

Turning now to FIGS. 4-6, a flowchart illustrating a method 400 for determining and correcting for misalignment of a phantom according to a first embodiment of the present disclosure is shown. At least some aspects of the method 400 may be carried out according to instructions stored in memory and executed by one or more processors of an imaging system, such as computing device 216 of imaging system 200. In some examples, one or more aspects of the method 400 may be carried out manually by a user. In some examples, the method 400 may be performed in real-time.

At 402, method 400 includes aligning a fiducial mark of the phantom with laser guides of the imaging system. Placement of the phantom on the table, aligned based on the fiducial mark and the laser guides may be executed manually by the operator. For example, the phantom that is placed on the table (e.g., in direct face sharing contact with the table) may include a fiducial mark that is positioned in the center of the phantom or alternatively at an edge of the phantom. The fiducial mark may aid in initial alignment of the phantom by the user, as the user may align the fiducial mark with the laser guides corresponding to a position of an isocenter of the imaging system. The laser guides may indicate the isocenter in each of the x, y, and z-axes.

At 404, method 400 includes receiving a scan acquisition request. The scan acquisition request may be received via user input to an operator console of the imaging system, such as operator console 220 of imaging system 200. In some examples, the operator console may include a user input device, such as a keyboard, a touchscreen, or the like, through which the user may input the scan request. In some examples, a phantom may be placed atop a table of the imaging system (e.g., table 114), for example in direct face sharing contact with the table, in a designated holder, or in an accessory slot. The scan acquisition may be initiated under designated parameters for scanning the phantom. For example, initiating the scan request may include identification of the type of phantom that is present.

At 406, method 400 includes acquiring scan data. As noted, the scan acquisition may be executed according to a predefined protocol. The scan acquisition may include one or more image views. For example, one or more of an axial scan, or a sagittal scout scan, and/or a coronal scout scan may be performed.

At 408, method 400 includes determining whether the scan is valid. A scan may be determined to be valid if a center row of the scan is sufficiently obstructed by an object (e.g., a portion of the phantom). Since the X and Y center algorithm, as will be further described below, uses center row, if the center row are not obstructed by any portion of the phantom, the process of centering will not provide a usable output. Thus, center row may be checked for sufficient obstruction. If valid (e.g., there is sufficient obstruction), method 400 proceeds to 410. If invalid (e.g., there is insufficient obstruction), method 400 ends.

At 410, method 400 includes extracting scan views at 180 and 90 degrees. In some examples, the scan acquisition may include acquisition of one or more views, for example the axial scan has multiple views as a function of rotational angle. For example the sagittal and coronal views, may be extracted from the data acquired in the axial scan. The 180 degrees (coronal) extracted view and the 90 degrees (sagittal) extracted view may allow for determination of distances to the isocenter in the y and x-directions. Extraction of additional scan views may be executed by the image reconstructor of the imaging system, in some examples. In other example, two scout scans at 180 and 90 degree, respectively, can be used for 180 and 90 degree views as well.

At 412, method 400 determines whether the phantom entirely obstructs the field of view of the imaging system in the x direction, which means that the phantom covers all detector pixels and so attenuate x-ray uniformly except a slight angle dependence due to a fan x-ray beam. So, a homogeneous image indicates no exposed area due to a misalignment. In examples in which the phantom entirely obstructs the view, the phantom may be centered with respect to the x and y directions. In examples in which the phantom does not entirely obstruct the view, for example when the field of view of the scan acquisition includes non-phantom material, the phantom may not be centered in one or both of the x and y-direction. If the phantom entirely obstructs the view in the x-direction, method 400 proceeds to 414 (see FIG. 5). If the phantom does not entirely obstruct the view in the x-direction, method 400 proceeds to 420 (see FIG. 6).

Continuing with FIG. 5, at 414, in response to determination that the phantom entirely obstructs the view in the x-direction, method 400 includes locating the phantom edges in the z-direction. Locating the edges of the phantom in the z-direction may include analyzing x-ray scan data from a scout or an axial scan to determine homogeneity or a uniform phantom area. A uniform thickness phantom shows a uniform x-ray attenuation in a scan image. In contrast, the different thicknesses of a phantom or table or air without any phantom each have very different x-ray attenuation. Therefore, the edge of a uniform area can be searched by looking at a sudden drop or increase in the x-ray attenuation in the image. Determining homogeneity or uniform phantom area may define whether the phantom is centered at the isocenter with respect to the z-axis since the width of the phantom is known. If the phantom is not centered at the isocenter, obstructed vs unobstructed regions of the phantom in the z-direction may be determined by searching a sudden change in x-ray attenuation in the scan image. Based on the locations of the obstructed and unobstructed regions, the edges of the phantom in the z-direction may be located.

At 416, method 400 includes determining a first distance to the isocenter in the z-direction. The first distance may be the z-distance and may include both a magnitude and direction (e.g., negative or positive) of movement. For example, a positive movement may indicate that the table is to be moved further into the gantry while a negative movement may indicate that the table is to be moved further out of the gantry. The magnitude may be determined within a predefined threshold. For example, the distance may be computed more precisely than is executable by movement of the table. As a non-limiting example, the distance may be computed to a tenth of millimeter while the table may move in millimeter, in its most precise movement. Thus, the outputted first distance may be outputted within the threshold of the movement capabilities of the table, for example to the millimeter in the example provided.

At 418, method 400 includes operating the table motor controller based on instructions from the computing device to move the phantom the first distance. The table motor controller, as described with respect to FIG. 2 may be configured to adjust the position of the table with respect to the gantry. The table motor controller may thus be operated to move the table the first distance in the z-direction. In some examples, the movement of the table may be performed in response to the output of the first distance as computed in an automated manner without user input.

Continuing to FIG. 6, at 420, in response to determination that the phantom does not entirely obstruct the view in the x-direction, method 400 includes determining if both phantom edges are visible. In some examples, the edges in the x-direction may be identified within the 180 degree extracted view. Determining whether the edges in the x-direction are visible may include analyzing x-ray scan data from the 180 degree extracted view to determine homogeneity or a uniform phantom area. A uniform thickness phantom shows a uniform x-ray attenuation in a scan image.

In contrast, the different thicknesses of a phantom or table or air without any phantom each have very different x-ray attenuation. Therefore, the edge of a uniform area can be searched by looking at a sudden drop or increase in the x-ray attenuation in the image. If a sudden drop is detected, an edge may be visible. If both phantom edges are visible, the phantom may not be centered along the y-axis (e.g., may be positioned too close to the detector such that the phantom is not covering the whole detector) and may or may not be centered along the x-axis. If both the phantom edges are not visible, the phantom may be centered in the y-direction but not in the x-direction. If both phantom edges are visible, method 400 proceeds to 424. If both phantom edges are not visible, method 400 proceeds to 422.

At 422, method 400 includes determining a second distance in the x-direction. When both phantom edges in the x-direction are not visible, for example if one of the x-edges is visible and the other is not or if both of the x-edges are not visible, the second distance in the x-direction may be calculated based on the length of exposed area and the design margin of the x-width of the phantom, as known to the system. When both edges are not visible, the phantom can be assumed to be aligned within the phantom design margin. Following 422, method 400 proceeds to 430, as will be described below.

At 424, in response to determination that both x-edges of the phantom are visible within the image, method 400 includes determining whether the phantom is centered in the x-direction. When both the x-edges are visible, the phantom may not be centered in the y-direction and may or may not be centered in the x-direction, as noted above. Determining whether the phantom is centered in the x-direction may include identifying a center of the phantom along the x-axis. Identifying the center of the phantom along the x-axis may include identifying the position of the two x-edges by measuring the exposed area length. A midway point between the positions of the two x-edges may be the position of the center in the x-direction. If the center in the x-direction aligns with the isocenter of the imaging system, the phantom may be centered in the x-direction. If the center of the phantom in the x-direction does not align with the isocenter of the imaging system, the phantom may not be centered in the x-direction. If centered, method 400 proceeds to 428. If not centered, method 400 proceeds to 426.

At 426, method 400 includes determining the second distance in the x-direction. When the x-edges are visible in the image, determining the second distance in the x-direction may include determining a distance between the center of the phantom in the x-direction and the isocenter. The distance between the center of the phantom in the x-direction and the isocenter may be the second distance.

At 428, method 400 includes determining a third distance in the y-direction. Determining the third distance in the y-direction may include finding edges of the phantom in the y-direction in the scan images or in the 90 degree view. For example, the 180 degree extracted view may be used for determining of x-edges and the 90 degree view may be used for determining y-edges. As explained above with respect to locating the edges in the z-direction and determining whether edges in the x-direction are present, locating edges in the y-direction may include analyzing x-ray scan data from the 90 degree extracted view to determine homogeneity or a uniform phantom area or the axial scan images. A uniform thickness phantom shows a uniform x-ray attenuation in a scan image. In contrast, the different thicknesses of a phantom or table or air without any phantom each have very different x-ray attenuation. Therefore, the edge of a uniform area can be searched by looking at a sudden drop or increase in the x-ray attenuation in the image. Determining homogeneity or uniform phantom area may define the location of the edges in the y-direction.

With the edges in the y-direction located, a center in the y-direction can be determined, as explained above with respect to determining the center in the y-direction, and the third distance in the y-direction to the isocenter may be determined based on the position of the center in the y-direction.

The first and second distances may indicate the amount of lateral misalignment, wherein lateral misalignment includes misalignment within the x-z plane. The third distance may indicate the amount of vertical misalignment. In some examples, one or more of the first, second, and third distances may be zero, indicating that the phantom is adequately aligned in the corresponding direction. For example, for step phantoms, a table position in the y-direction may be predefined and thus the computed third distance in the y-direction may be zero.

The second and third distances may be outputted to the computing device of the imaging system as well as to the operator console of the imaging system, in some examples. For example, the first, second, and third distances may be outputted to the computing device in order for automated movement of the table to be executed therefrom. The second and third distances may also be outputted to the operator console (e.g., to a display device of the operator console) in order for the user to review the computed distances.

At 430, method 400 includes operating the table motor controller to move the phantom (e.g., the phantom on the table) in the second and/or third distances. In some instances, the imaging system may be equipped with a table motor controller configured to move the table in the z and y directions but not the x-direction. In other instances, the imaging system may be equipped with a table motor controller to move the table in all of the x, y, and z directions. The table motor controller, as described with respect to FIG. 2 may be configured to adjust the position of the table with respect to the gantry. The table motor controller may thus be operated to move the table the second distance in the x-direction and/or the third distance in the y-direction. If the phantom is centered in the y-direction, the table motor controller may be operated to move the phantom in the second distance (if automated movement in the x-direction is available) but not in the y-direction. If the phantom is not centered in the y-direction, the table motor controller may be operated to move the phantom the second distance (if automated movement in the x-direction is available) and the third distance. In this way, the movement of the table may be performed in response to the output of the distances as computed in an automated manner without user input. If automated movement in the x-direction is not available, the table may be moved the second distance manually by the operator.

In some examples, following centering of the phantom in the x and y directions, the method 400 may return to 414 to determine centering movement needed in the z-direction, as described above. Thus, the phantom may be moved in the x-direction, the y-direction, and the z-direction, as needed based on determinations of positions of the phantom, in an automated manner.

At 432, method 400 includes repeating scan acquisition. The scan acquisition may be performed with the phantom in the new, centered position. Confirmation of the centered position may be performed, in some examples, via the same procedures described above for determining amount of misalignment. The repeated scan acquisition, with the phantom centered with the isocenter of the system, may thus be used for calibration of the imaging system.

In this way, the phantom may be automatically centered to align with the isocenter of the imaging system from any initial position. For example, the user may place the phantom on the table, for example in a designated mount, arbitrarily and the system may calculate the distances needed to move the table in order to center the phantom and may operate the table motor controller to align the phantom at the isocenter. Thus, human error of phantom misalignments as may occur with manual alignment with laser guides may be mitigated, providing increased accuracy of the calibration scan. Further, need for manual repositioning and repeated acquisitions as a result of misalignment of the phantom may be reduced, saving time and user effort.

Turning now to FIG. 7, a flowchart illustrating a method 700 for determining and correcting for an amount of misalignment of a phantom according to a second embodiment of the present disclosure is shown. At least some aspects of the method 700 may be carried out according to instructions stored in memory and executed by one or more processors of an imaging system, such as computing device 216 of imaging system 200 described with respect to FIG. 2 above. In some examples, one or more aspects of the method 700 may be carried out manually by a user. In some examples, the method 700 may be performed in real-time during collection of calibration data. In some examples, method 700 of the second embodiment may apply to layered slab phantoms, step phantoms, and the like that includes multiple different regions.

At 702, method 700 includes receiving a request to initiate a scan of a phantom placed on a table. In some examples, the phantom that is placed on the table (e.g., in direct face sharing contact with the table) may include a fiducial mark. The fiducial mark may be positioned in the center of the phantom or alternatively at an edge of the phantom. The fiducial mark may aid in initial alignment of the phantom by the user, as the user may align the fiducial mark with the laser guides corresponding to a position of an isocenter of the imaging system. The laser guides may indicate the isocenter in each of the x, y, and z-axes. In some examples, elevation of the table, and thus position of the phantom in the y-direction, may be predefined for a particular slab or step phantom, in which case the fiducial mark may be aligned with the laser guides in the z and x directions by the user and the phantom may be placed at the predefined table elevation in the y-direction.

At 704, method 700 includes acquiring the scan of a current step of the phantom. Each of the steps or layers of the phantom may be scanned individually in sequence, in some examples. A first step in the sequence of steps may be a first step along the z-direction, in some examples. As will be described herein, identification of misalignment may be performed iteratively for each step that is scanned. The current step, in a first iteration of the method, may be the first step in the sequence. In subsequent iterations, the current step may be subsequent steps of the phantom.

At 706, method 700 includes applying an edge finding algorithm to determine if edges of the current step of the phantom are out of view. If the phantom is properly aligned, all edges of the current step of the phantom may be within the field of view of the imaging system and thus the current step of the phantom may cover all detector pixels for x-ray attenuation. The phantom may be misaligned if any exposed detector pixels see x-rays without attenuation. Further, the phantom may be misaligned if a portion of the detector covers a next step of the phantom. As described with respect to method 400, the edge finding algorithm may comprise analyzing x-ray scan data to determine homogeneity or a uniform phantom area. A uniform thickness phantom shows a uniform x-ray attenuation in a scan image. In contrast, the different thicknesses of a phantom or table or air without any phantom each have very different x-ray attenuation. Therefore, the edge of a uniform area can be searched by looking at a sudden drop or increase in the x-ray attenuation in the image. Determining homogeneity or uniform phantom area may define the location of the edges and thus allow for determining if the edges are in view or out of view.

At 708, method 700 includes determining, based on the edge finding algorithm applied at 706, whether all edges are in view. Similar to as described above, edges being in view may indicate presence of lateral misalignment. If no edges are in view, the phantom may be centered laterally. If the edge finding algorithm detects that the edges out of view (NO at 708), method 700 proceeds to 712. If the edge finding algorithm detects any edges in view (YES at 708), method 700 proceeds to 710.

At 710, method 700 includes determining the amount of lateral misalignment. Lateral misalignment may refer to misalignment of the phantom in the x-z plane. For example, misalignment left and right (e.g., in the x-direction) and in and out of the gantry (e.g., in the z-direction) may be determined. The amount of lateral misalignment may be determined based on the edge finding algorithm. As an example, distances between the position of the detected edge of the phantom and the position of the edge of the exposed detector pixels may be used to determine the lateral misalignment. As another example, the edge finding algorithm may include determining a position of the center of the phantom, which may be compared to the position of the isocenter to determine lateral misalignment. The amount of lateral misalignment may thus indicate distances to alignment in one or more directions.

At 712, method 700 includes determining if the phantom is left/right leveled on the table. Determining if the phantom is left/right leveled may comprise determining an average count of the left and right-most pixels. If more pixels are present in the left-most pixel count than the right-most pixel count, the phantom may be determined to be tilted to the left. Similarly, if more pixels are present in the right-most pixel count than the left-most pixel count, the phantom may be determined to be tilted to the right. If the phantom is left/right level (YES at 712), method 700 proceeds to 716. If the phantom is not left/right level (NO at 712), method 700 proceeds to 714.

At 714, method 700 includes determining an amount of tilt misalignment. As noted at 712, tilt misalignment may be detected when pixel counts of the left and right-most pixels are unequal. The difference between the pixel counts may thus indicate the amount of tilt misalignment, wherein a greater discrepancy corresponds to more tilt. The amount of tilt misalignment may thus generate an amount of tilt to alignment (e.g., a rotation to level amount).

At 716, method 700 includes adjusting a position of the table to align the phantom. The position of the table may be adjusted based on the amount of tilt misalignment (e.g., the determined amount of rotational to level as determined at 714) and the amount of lateral misalignment (e.g., the lateral distances to alignment as determined at 710). Similar to as described with respect to method 400, adjusting the position of the table may be entirely automated, partially automated, or in some examples, entirely manual. For example, the table motor controller may control movements of the table in all of the x, y, and z-directions, including rotation about one or more of the axes (e.g., rotation about the z-axis) automatically in response to determination of amount of lateral misalignment and amount of tilt misalignment. As noted, a position of the phantom (and thus the table) in the y-direction may be predefined for the particular slab or step phantom being used. In such examples, the determined amount of tilt to alignment and the lateral distances to alignment may be outputted to the computing device so as to then instruct the table motor controller to adjust the position of the table based thereon.

In some examples, adjustment of the position of the table may not include movements in the y-direction when the elevation of the table is already at the predefined position. In other examples, adjustment of the position of the table may include movement of the table in the y-direction to reach the predefined position. Further, in some examples, automated movements in one or more of the directions, such as the x-direction, may be unavailable. In such examples, automated movement may be executed for the other directions and movement of the one or more of the directions for which automated movement is unavailable may be performed manually by the user. In those examples, the automated movement amounts may be outputted to the computed device similar to as above and the manual movement amounts may be outputted to the operator console for the user to view. In yet further examples, automated movement in all directions may not be available, in which case the user may execute the movements manually via the table motor controller and/or gantry controller. The movement amounts may be outputted to the operator console in such examples for the user to view and act thereon.

At 718, method 700 determines whether there is a subsequent step of the phantom. As noted, the step or slab phantoms may comprise a plurality of steps or layers, respectively. Each step or layer may be imaged in sequential acquisitions (or is sequential portions of the acquisition). If a subsequent phantom step is to be imaged (YES at 718) method 700 returns to 704, after moving the table in the z direction for the designed step width, to acquire scan data of the current step of the phantom. The subsequent phantom step may thus be the current step and the method 700 may proceed as described above. In this way, the method 700 may be executed repeatedly for each step of the phantom in order to ensure proper alignment of the phantom at each step.

Proper alignment of the phantom, including proper alignment of each step or layer of the phantom when the phantom is a step or slab phantom, may thus ensure accurate calibration of the imaging system. Phantoms, as described above, include imageable materials of different densities with known and repeatable x-ray attenuations maps allowing for calibration of the imaging system. Misaligned phantoms may produce inaccurate results, thus meaning that calibration based thereon may be inaccurate. The methods described above check and correct for misalignment, increasing the accurate of calibration of the imaging system and decreasing the need for repeated calibration acquisitions.

Figure 8:
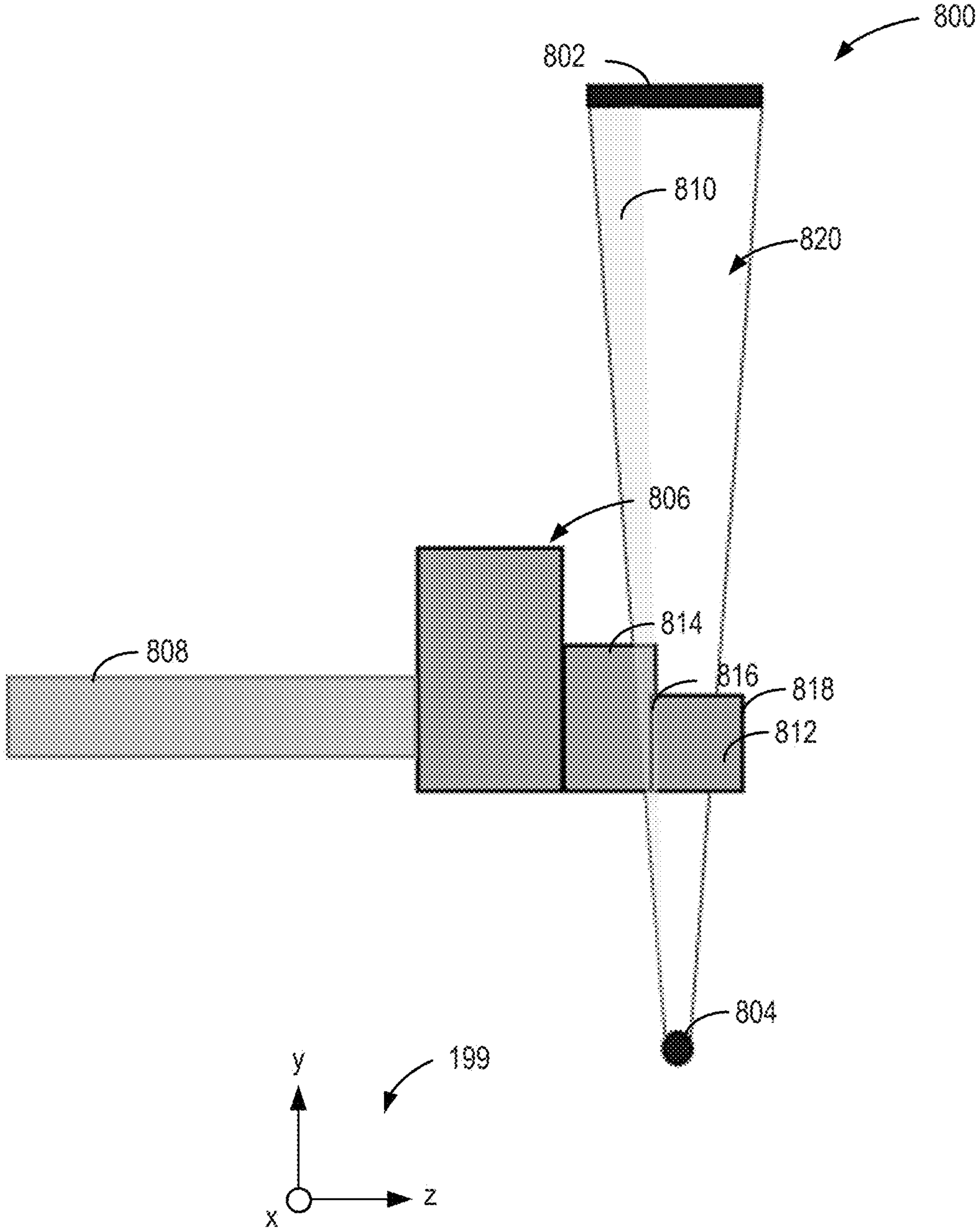
FIG. 8 shows a first exemplary phantom misalignment.
Figure 9:
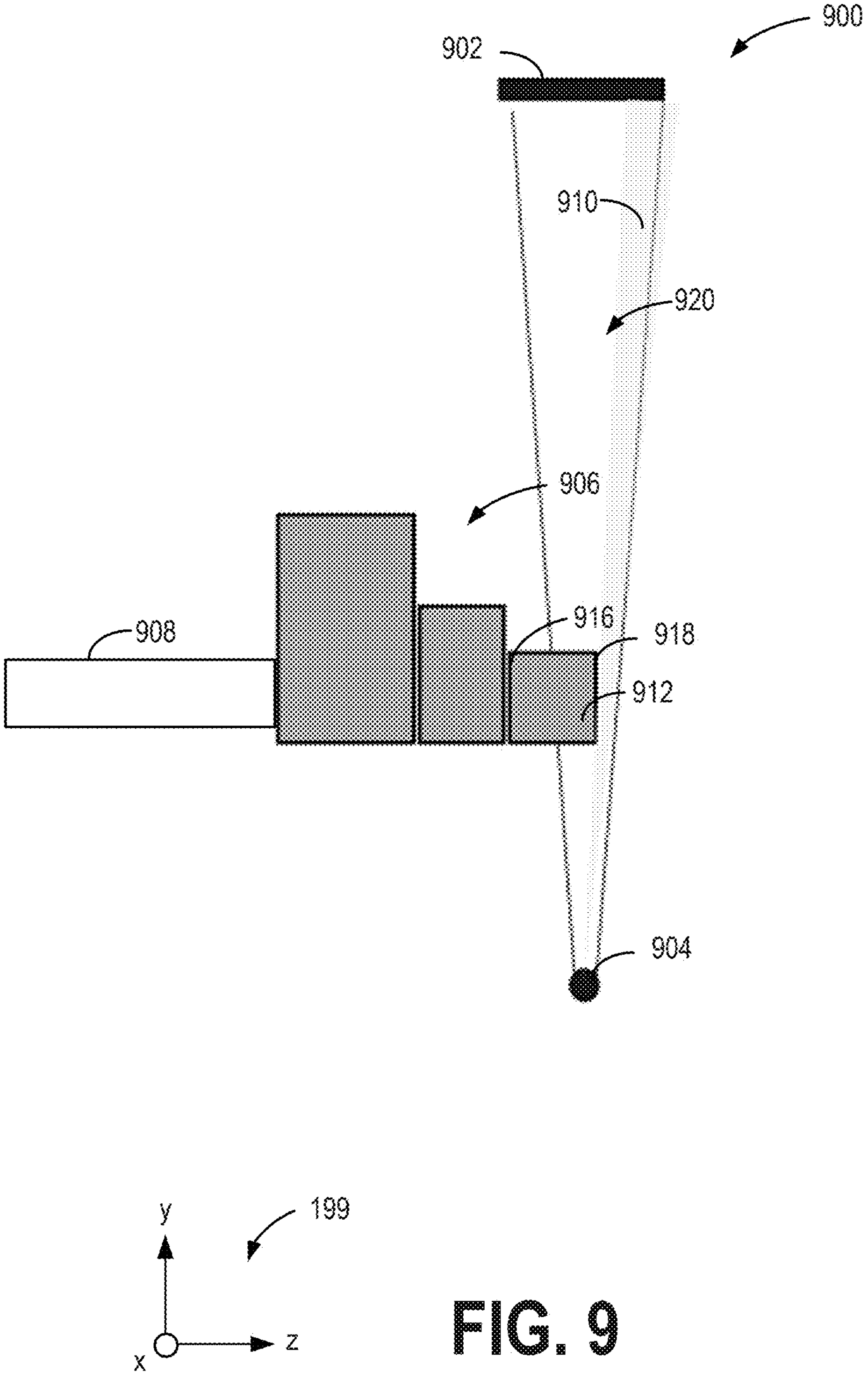
FIG. 9 shows a second example phantom misalignment.
Figure 10:
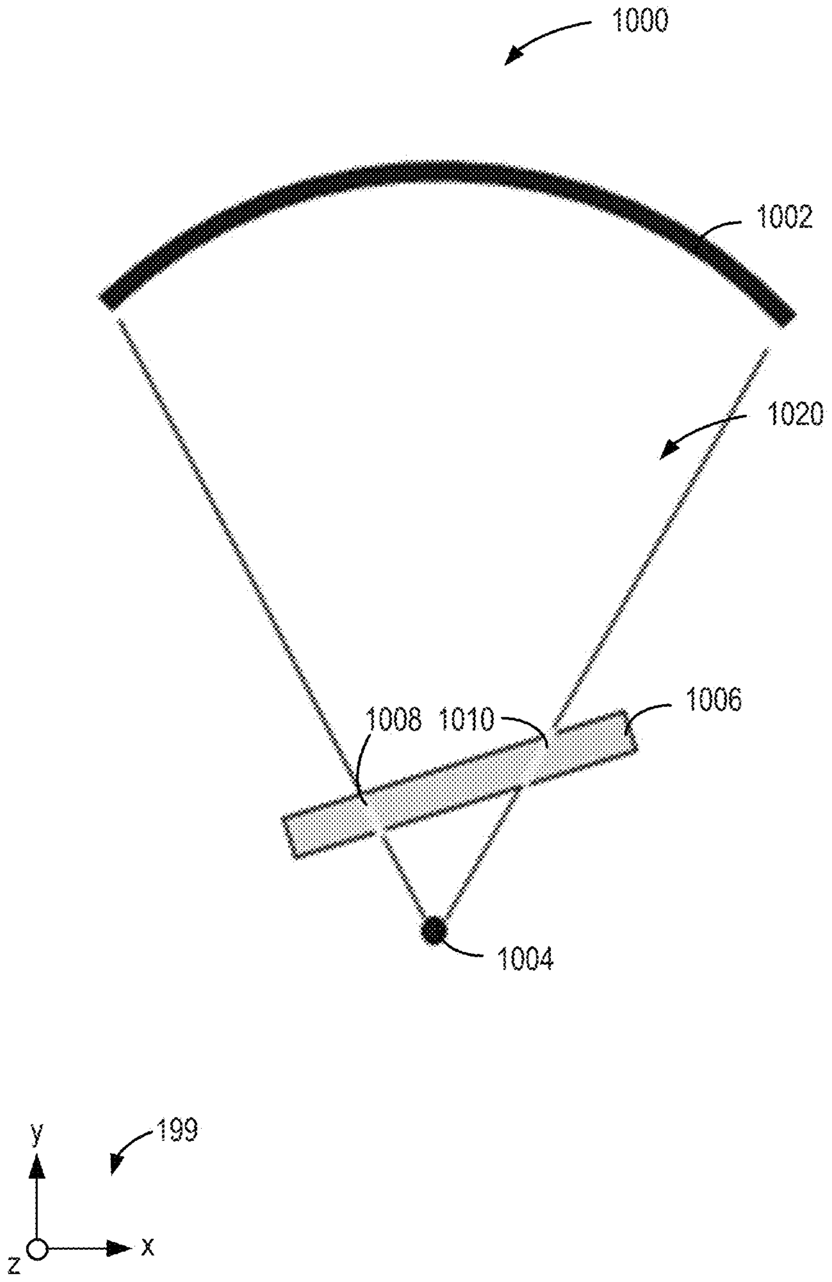
FIG. 10 shows a third example phantom misalignment.

Turning now to FIGS. 8-10, various examples of phantom misalignment are shown. For example, FIGS. 8 and 9 specifically show lateral phantom misalignment and FIG. 10 specifically shows tilt misalignment.

Starting with FIG. 8, a first phantom misalignment example 800 is shown. In the first phantom misalignment example 800, a phantom 806 is a step phantom. For example, a detector 802 of an imaging system may be positioned opposite an x-ray focal spot 804. X-rays may be emitted from the x-ray focal spot 804 towards the detector 802, passing through the phantom 806. The phantom 806 may comprise a plurality of steps, for example a first step 812 and a second step 814 positioned adjacent to each other with respect to the z-axis. The phantom 806 may be positioned at the end of a table 808 through a mounting hole located at the end of the table.

A beam of radiation 820 may define volume of coverage where x-rays emit from the x-ray focal spot 804 towards the detector 802. The phantom 806 may intersect with the beam of radiation 820. The position of the table 808 and the phantom 806 thereon may affect where the intersection is and thus whether any of the phantom is outside the field of view. For example, the phantom 806 may be positioned such that the first step 812 is positioned within the beam of radiation 820. Lateral misalignment of the phantom 806 with respect to the z-axis, in the first phantom misalignment example 800, may result in a portion of the first step 812 being outside the beam of radiation 820 and a portion of the second step 814 being inside the beam of radiation 820.

As described above, edges of the phantom, and in particular edges of the first step 812 of the phantom in the example of a step phantom, may be identified. For example a first edge 816 and a second edge 818 may be identified. The first edge 816 and the second edge 818 may be z-axis edges. Determination of the position of the first edge 816 may indicate that the first edge 816 is within the beam of radiation 820 and the second edge 818 is in the distance of the designed step phantom width from the first edge 816 outside the beam of radiation 820. Further, the first edge 816 may also be an edge of the second step 814, and a portion 810 of overlap in the beam of radiation 820 where the second step 814 resides within the beam of radiation 820 as well.

The positions of the first and second edge 816, 818 with respect to the position of the beam of radiation 820 may thus allow for determination of a table movement in the x-direction to align the phantom (e.g., the first step 812). FIG. 8 thus shows a first type of misalignment with respect to the z-axis, whereby the phantom is positioned too far into the gantry of the imaging system and thus movements to align the phantom determined based on the position of the phantom may include moving the position along the z-axis out of the gantry.

It should be understood that while a step phantom is herein shown, other types of phantoms may also be used without departing from the scope of this disclosure. Further, it should be understood that edges may be identified in other directions not shown in FIG. 8 and that instead of edges for some axes, a center may be found. For example, edges in the z-direction of a non-step or slab phantom may be identified and a center in the x-y plane may be identified, as described with respect to FIGS. 4-6 and as is described in FIG. 7, edges may be found in the x-direction as well.

Turning now to FIG. 9, a second phantom misalignment example 900 is shown. In the second phantom misalignment example 900, a phantom 906 is a step phantom. For example, a detector 902 of an imaging system may be positioned opposite an x-ray focal spot 904. X-rays may be emitted from the x-ray focal spot 904 towards the detector 902, passing through the phantom 906. The phantom 906 may comprise a plurality of steps, for example a first step 912. The phantom 906 may be positioned in face sharing contact with a table 908.

A beam of radiation 920 may define the volume of coverage where x-rays emit from the x-ray focal spot 904 towards the detector 902. The phantom 906 may intersect with the beam of radiation 920. The position of the table 908 and the phantom 906 thereon may affect where the intersection is and thus whether any of the phantom is outside the field of view. For example, as shown, the phantom 906 may be positioned such that the first step 912 is positioned partially within the beam of radiation 920. Lateral misalignment of the phantom 906 with respect to the z-axis, in the second phantom misalignment example 900, may result in a portion of the first step 912 being outside the beam of radiation 920.

As described above, edges of the phantom, and in particular edges of the first step 912 of the phantom in the example of a step phantom, may be identified. The position of the first step 912, with a second edge 918 within the beam of radiation 920 and a first edge 916 outside the beam of radiation 920, may thus result in a portion 910 of the beam of radiation 920 having unattenuated x-rays. The attenuation difference due to the partial illumination can be used first to identify the second edge 918. Even though the first edge 916 is out of the beam 920, since the phantom step has a known width from an engineering design, the first edge 916 location can be estimated from the location of the second edge 918 in the detector signal.

The positions of the first and second edge 916, 918 with respect to the position of the beam of radiation 920 may thus allow for determination of a table movement in the x-direction to align the phantom (e.g., the first step 812). FIG. 9 thus shows a second type of misalignment with respect to the z-axis, whereby the phantom is positioned not far enough into the gantry of the imaging system and thus movements to align the phantom determined based on the position of the phantom may include moving the position along the z-axis more into of the gantry.

Turning now to FIG. 10, a third phantom misalignment example 1000 is shown. A detector 1002 of an imaging system may be positioned opposite an x-ray focal spot 1004. X-rays may be emitted from the x-ray focal spot 1004 towards the detector 1002, passing through a phantom 1006.

A beam of radiation 1020 may define the volume of coverage where x-rays emit from the x-ray focal spot 1004 towards the detector 1002. The phantom 1006 may intersect with the beam of radiation 1020. Tilt of the phantom 1006 about the z-axis may result in different pixel counts of the left and right most pixels. For example, a first portion 1008 of the phantom 1006 may correspond to left-most pixels in an acquired image thereof and a second portion 1010 of the phantom 1006 may correspond to right-most pixels in the acquired image. The first portion 1008 may intersect at a first angle that results in a first pixel count and the second portion 1010 may intersect at a second angle that results in a second pixel count. The second pixel count, in some examples, may be smaller than the first pixel count due to the x-ray pathlength difference between 1008 and 1010. A difference in the first and second pixel counts may indicate how much the phantom 1006 is tilted, based on the known parameter of the beam of radiation 1020.

According to Bee-Lambert law, the path length of 1008 and 1010 can be measured using $I=I_o \exp^{(\mu^* x)}$, where $I_o$ is the incident x-ray flux count, I is the measured count, μ is an attenuation coefficient mostly dependent on the step phantom material and x-ray energy, and x represents path length. Once the path length of 1008 and 1010 gets calculated, the tilt angle can be estimated. The first and second pixel counts and the difference therebetween may thus allow for determination of an amount of tilt or z-axis rotation of the phantom. For example, in the third phantom misalignment example 1000 shown in FIG. 10, the tilt to center may include rotating the phantom clockwise about the z-axis to bring the second portion 1010 down and/or the first portion 1008 up, thus leveling the phantom 1006.

Figure 11:
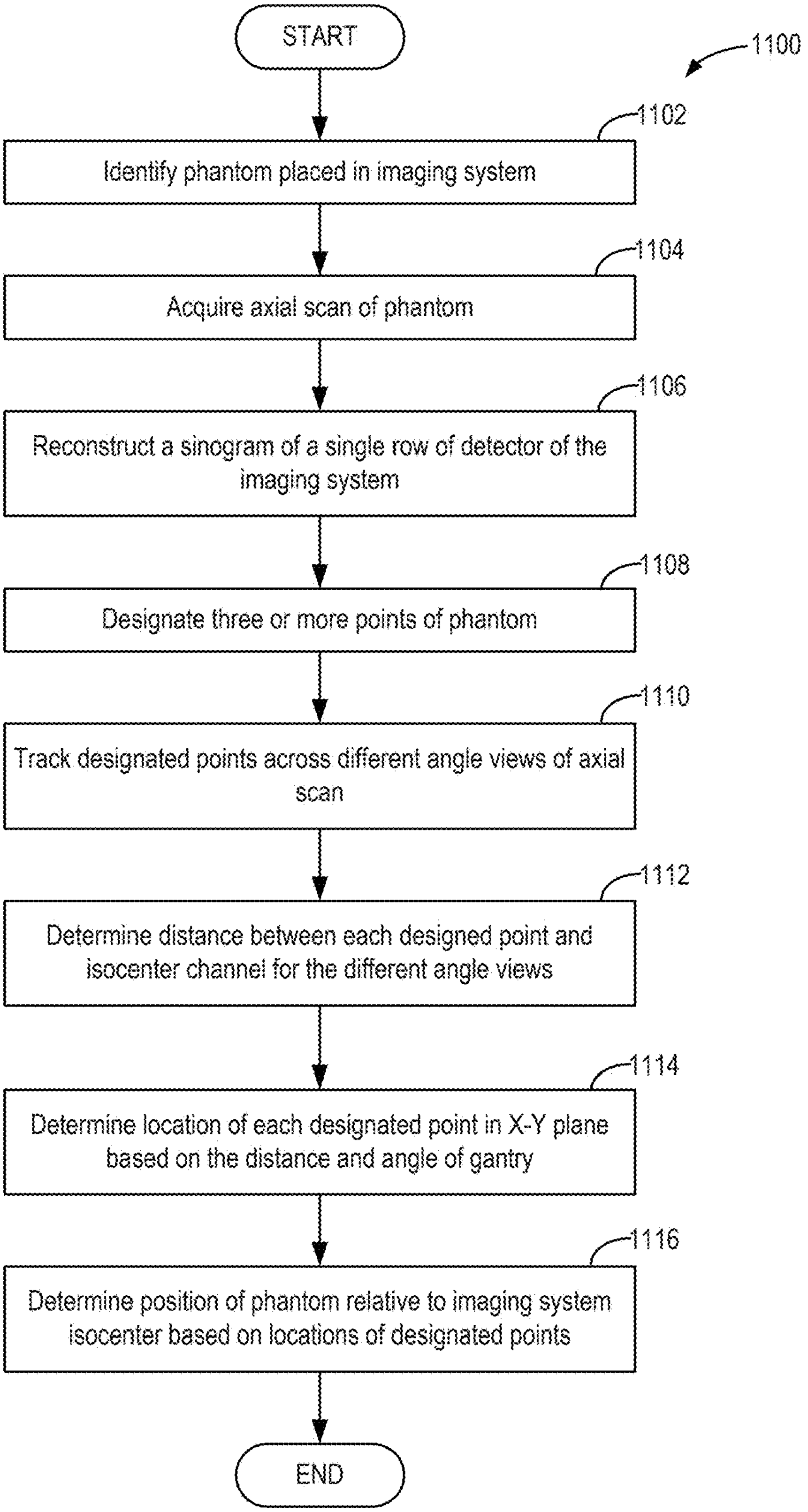
FIG. 11 shows a flowchart illustrating a method for determining centering distances for an imaging system according to a third embodiment.

FIG. 11 shows a flowchart illustrating a method 1100 for determining amount of misalignment in the x and y directions according to a third embodiment of the present disclosure. At least some aspects of the method 1100 may be carried out according to instructions stored in memory and executed by one or more processors of an imaging system, such as computing device 216 of imaging system 200 described with respect to FIG. 2 above. In some examples, one or more aspects of the method 1100 may be carried out manually by a user. In some examples, the method 1100 may be performed in real-time during collection of calibration data. In some examples, method 1100 of the second embodiment may apply to layered slab phantoms, step phantoms, and the like that includes multiple different regions, though it should be understood that the method may be applied to any type of phantom.

At 1102, method 1100 includes identifying a phantom placed in an imaging system. In some examples, a scan initiation request, based on user inputs to an operator console of the imaging system, may include an identification of type of phantom to be imaged. For example, in some examples, the user may input, via selection in a drop down menu, a search query, or the like. In another example, the phantom may be identified using RFID confirmation or with the patient positioning camera of the imaging system. In case of a step phantom, the phantom placed by the user can be electronically matched between the user input and the RFID attached to the phantom to confirm a matching phantom is placed in the gantry. In other examples, the user may select a particular calibration scan protocol, which may correspond to and thereby identify, a phantom to be imaged. The slab or step phantom as herein considered may be placed in a bore of the imaging system.

At 1104, method 1100 includes acquiring an axial scan of the phantom. As noted, the scan acquisition may be executed according to a predefined protocol.

At 1106, method 1100 includes reconstructing a sinogram of a single row of the detector of the imaging system. The sinogram may be a 2D image that shows the raw data of the axial scan (e.g., raw data prior to image reconstruction algorithms are applied by the image reconstructor). For example, projection data acquired during acquisition of the axial scan may be organized into a 2D array, where one axis represents an angle of the projection and the other axis represents the position along the detector. For example, the sinogram may be described by views on the x-axis and channels on the y-axis.

At 1108, method 1100 includes designating three or more points of the phantom. The points may be an arbitrary pixel or group of pixels of the phantom as imaged. For example, the points may each be at an edge, aligned with a fiducial marker, at a center, or any other point of the phantom. In some examples, the points may each be designated at a different edge of the phantom, such that each point is adjacent to air and is otherwise not obstructed by the rest of the body of the phantom, however it should be understood that the points can be any point of the phantom. In some examples, the phantom may be a 3D object, thus at least three points may be designated in order to determine orientation and position of the phantom.

At 1110, method 1100 includes tracking the designated points across different angle views of an axial scan. The axial scan may be transposable to sinogram space, in some examples. The designated point may not be visible in some views and may be visible in others, thus the point may come in and out of the sinogram space.

Figure 12A:
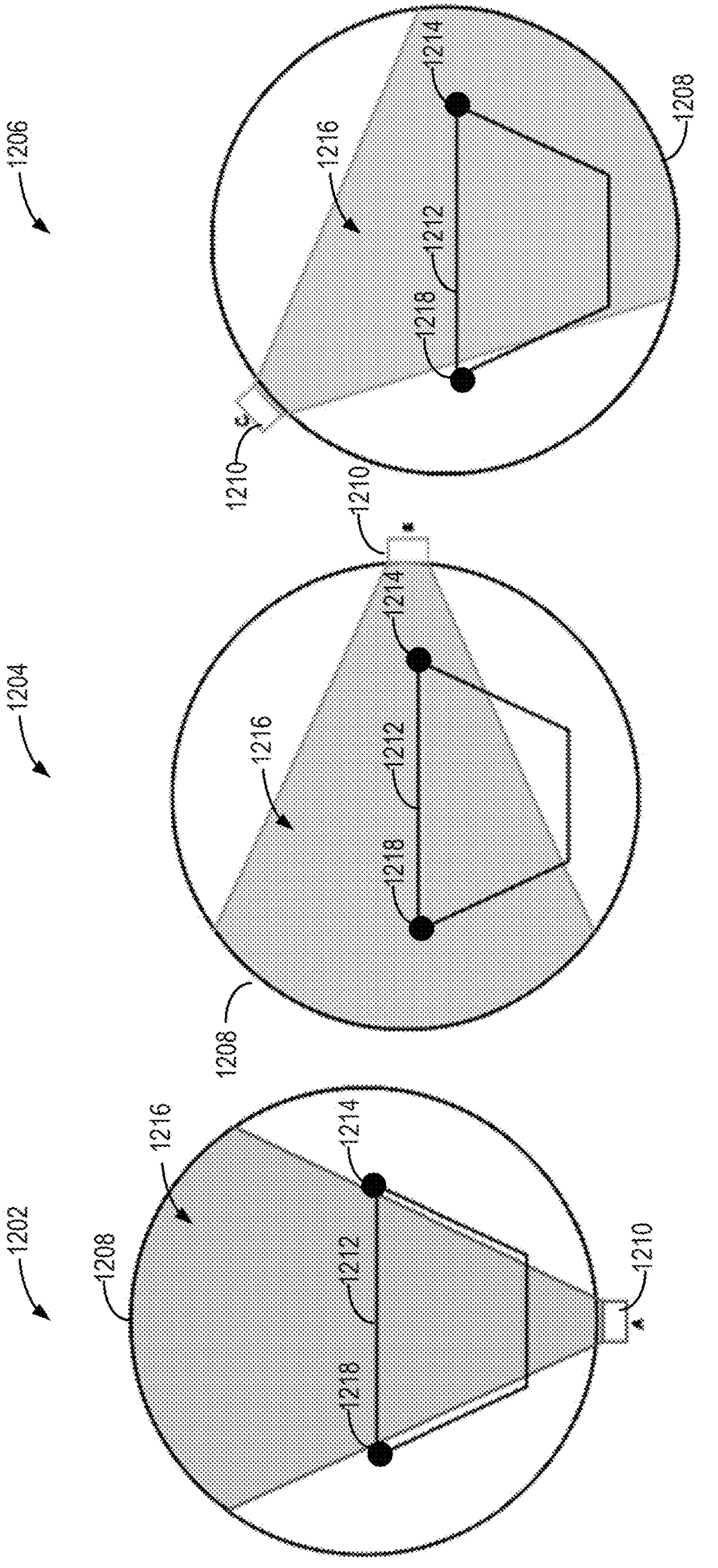
FIG. 12A shows diagrams of different angle views of an imaging system including designated points of a phantom.

Turning briefly to FIG. 12A, example diagrams of different angle views of an axial scan of a phantom are shown. For example, a phantom 1212 may be positioned in an imaging system between an x-ray source 1210 and a detector 1208. A beam of radiation 1216 may be emitted from the x-ray source 1210, pass through the phantom 1212, and attenuate upon the detector 1208. A first point 1214 of the phantom 1212 and a second point 1218 may be designated as herein described. The first and second points 1214, 1218 may be within the same plane of the phantom. As noted, three or more points are to be designated. As such, a third point of the phantom 1212, not depicted in FIG. 12A or FIG. 12B, may be designated in a different plane of the phantom.

In a first angle view 1202, the first point 1214 and the second point 1218 may be locations that are outside the beam of radiation 1216, and therefore outside a field of view of the imaging system. When outside the field of view, a point may be out of the sinogram space. In a second angle view 1204, the first point 1214 and the second point 1218 may both be in locations that intersect with the beam of radiation 1216 and therefore the points may be within a field of view of the imaging system. In a third angle view 1206, the first point 1214 may be in a location that intersects with the beam of radiation 1216 while the second point 1218 may be in a location that lies outside the field of view of the imaging system. Therefore, the first point 1214 may be within the field of view of the imaging system and thus in the sinogram space while the second point 1218 may not. As explained below, any two angle view data like first angle view 1204 and second angle view 1206 can be used to calculate the exact location of the designated points 1214 and 1218.

Returning to FIG. 11, at 1112, method 1100 includes determining a distance between the designated points and the geometric isocenter channel for each of the different angle views. In some examples, the distance between a designated point and the isocenter channel may be determined for angles when the point is in sinogram space and not for when the point is out of sinogram space. An isocenter channel 1220 is naturally defined as the gantry geometric center channel since the x-ray tube and the detector are fixed in the gantry and so rotate together around the gantry geometric isocenter without change in their relative position. The distance between the designated point and the isocenter channel may be denoted by a perpendicular line as the shortest distance therebetween.

Figure 12B:
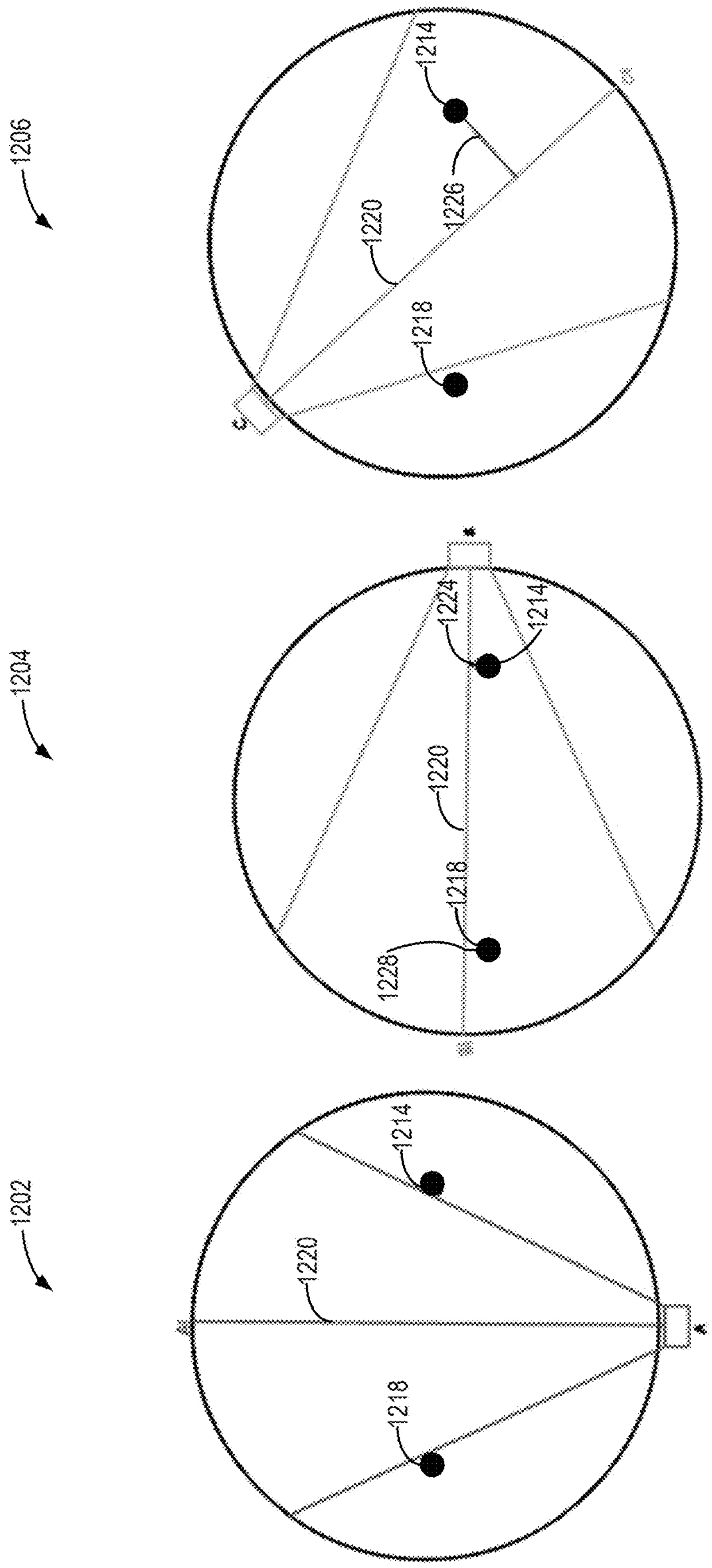
FIG. 12B shows the diagrams of FIG. 12B with distances between the designated points and a center channel.

Turning briefly to FIG. 12B, the example diagrams of FIG. 12A are again shown. As described, the isocenter channel 1220 of the imaging system may naturally be defined since the scanner gantry rotates around one fixed geometric center point. In some examples, as noted, when a designated point is within sinogram space, as in the second and third angle views 1204, 1206, the distance between the point and the isocenter channel 1220 may be determined. For example, a first distance 1224 may be determined between the first point 1214 and the isocenter channel 1220 and a second distance 128 may be determined between the second point 1218 and the isocenter channel 1220 with the phantom in position of the second angle view 1202. A third distance 1226 may be determined between the first point 1214 and the isocenter channel with the phantom in position of the third angle view 1208 but a distance may not be determined between the second point 1218 and the isocenter channel 1220 in the third angle view 1208 as the second point 1218 is out of sinogram space. Similarly, in the first angle view 1202, when both the first point 1214 and the second point 1218 are out of sinogram space, the distances may not be determined.

At 1114, method 1100 includes determining a location of the designated points in the x-y plane of the system. As each distance between one of the three or more designated points and the isocenter channel is known for any of two or more arbitrary views, the angle of the gantry may provide the angle of the scan view, thereby allowing for determination of the distance for that angle of the gantry. Thus, the location of the designated point may be determined based on the determined distance from the isocenter channel for that angle of the gantry. In summary, two angles and two distances may be used to calculate the x-y coordinate of each designated point.

At 1116, method 1100 includes determining the position of the phantom relative to the imaging system isocenter based on the location of the designated points. The position of the phantom relative to the isocenter may thus indicate distances in the x-direction and y-direction for which the phantom is to be moved to be centered. As explained above, outputting these determined distances may indicate automated movements to be made by the table motor controller in order to center the phantom with respect to the imaging system isocenter. As noted, the method 1100 may be directed towards determining misalignment in the x and y-directions, but not the z-direction. Determination of misalignment in the z-direction may be executed as explained above in the first or second embodiments.

In some examples, method 1100 may be performed once for a first designated point to determine lateral/vertical positioning of the phantom, thereby allowing for translational centering with respect to linear movements in the x and y-directions when the phantom is leveled. The method 1100 may be performed a second time for a second designated point to determine tilt or skew of the phantom, thereby allowing for automated rotational centering via rotation about the x or y axes. In other examples, the three or more designated points may enable both translational and tilt adjustment at the same time.

The technical effect of the systems and methods herein provided is that phantoms may be automatically centered during the calibration process. Identification and correction of misalignment of the phantom may ensure that the phantom is entirely and properly imaged. Proper imaging of the phantom may allow for more accurate calibration. By computing distances to center and automatically centering the phantom during calibration, misalignment may be corrected for. In this way, misalignment errors that may result from human error may be reduced. Further, time spent in repeating imaging and realigning the phantom manually may be reduced. Additionally, by automatically centering the phantom, processing power of the system for calibration scans may be reduced as need for repeated scans due to misalignment may be reduced.

The disclosure also provides support for a method for an imaging system, comprising: acquiring scan data of a phantom, determining one or more distances to a center of the imaging system of the phantom, and automatically adjusting a position of the phantom based on the one or more distances to center. In a first example of the method, determining the one or more distances to the center comprises: locating edges of the phantom, determining a first distance to center in the z-direction of the one or more distances to center, and determining second and third distances to center in an x-direction and a y-direction, respectively, of the one or more distances to center. In a second example of the method, optionally including the first example, automatically adjusting the position of the phantom based on the one or more distances to the center comprises adjusting a table of the imaging system the first distance to center in the z-direction, the second distance to center in the x-direction, and the third distance to center in the y-direction. In a third example of the method, optionally including one or both of the first and second examples, automatically adjusting the position of the phantom based on the one or more distances to the center comprises adjusting a table of the imaging system the first distance to center in the z-direction and the third distance to center in the y-direction. In a fourth example of the method, optionally including one or more or each of the first through third examples when the phantom is a step phantom, determining the one or more distances to the center comprises, for each step of the step phantom: applying an edge finding algorithm to the scan data, determining an amount of lateral misalignment of the step phantom in x and y directions, and determining an amount of tilt misalignment of the step phantom. In a fifth example of the method, optionally including one or more or each of the first through fourth examples, determining the amount of tilt misalignment comprises determining a difference between a first pixel count of left-most pixels and a second pixel count of right-most pixels. In a sixth example of the method, optionally including one or more or each of the first through fifth examples, the method further comprises: outputting the one or more distances to center to an operator console. In a seventh example of the method, optionally including one or more or each of the first through sixth examples, the imaging system is one of a photon counting computerized tomography (PCCT) system and a computerized tomography (CT) system.

The disclosure also provides support for a system, comprising: a computing device communicably coupled to an imaging system configured to image a phantom, the computing device configured with instructions in non-transitory memory that when executed cause the computing device to: identify the phantom to be imaged, acquire scan data of the phantom, determine amount of misalignment of the phantom in one or more directions, and automatically adjust a position of the phantom based on the amount of misalignment. In a first example of the system, identifying the phantom comprises one or more of receiving user input selecting the phantom from a menu of phantom options and radiofrequency identification tag (RFID) confirmation. In a second example of the system, optionally including the first example to determine the amount of misalignment of the phantom, the computing device is further configured with instructions stored in non-transitory memory that when executed cause the computing device apply an edge finding algorithm to determine position of edges of the phantom in a z-direction. In a third example of the system, optionally including one or both of the first and second examples, the scan data is an axial scan of the phantom and wherein the computing device is further configured with instructions that when executed, cause the computing device to extract scan views at 180 and 90 degrees. In a fourth example of the system, optionally including one or more or each of the first through third examples to determine the amount of misalignment of the phantom, the computing device is further configured with instructions stored in non-transitory memory that when executed cause the computing device to: finding and extracting the phantom from each of the scan views at 180 and 90 degrees, determining a position of a center of the phantom in an x-direction and a position of the center of the phantom in the y-direction, and comparing the position of the center of the phantom to an isocenter of the imaging system. In a fifth example of the system, optionally including one or more or each of the first through fourth examples to determine the amount of misalignment of the phantom, the computing device is further configured with instructions stored in non-transitory memory that when executed cause the computing device to: determine a first pixel count of left-most pixels of the scan data, determine a second pixel count of right-most pixels of the scan data, and determine a difference between the first and second pixel counts to determine tilt misalignment of the amount of misalignment. In a sixth example of the system, optionally including one or more or each of the first through fifth examples, the computing device is configured to automatically adjust the position of the phantom by adjusting a position of a table on which the phantom is placed in a z-direction and a y-direction via a table motor controller. In a seventh example of the system, optionally including one or more or each of the first through sixth examples, the computing device is additionally configured to automatically adjust the position of the table in an x-direction via the table motor controller. In a eighth example of the system, optionally including one or more or each of the first through seventh examples to determine the amount of misalignment of the phantom, the computing device is further configured with instructions in non-transitory memory that when executed cause the computing device to: reconstruct a sinogram of a single row of a detector of the imaging system, track three or more designated points of the phantom across different angle views of an axial scan, determine distances between each of the three or more designated points and an isocenter channel of the imaging system for each of the different angle views, based on the distances between each of the three or more designated points and the isocenter channel and an angle of a gantry of the imaging system, determine locations of each of the three or more designated points, and determine a position of the phantom relative to an isocenter of the imaging system based on the locations of the three or more designated points.

The disclosure also provides support for a method for automatically centering a phantom, comprising: acquire scan data of the phantom on a table with an imaging system, determine a first distance from a center of the phantom to an isocenter of the imaging system in a z-direction, determine a second distance from the center of the phantom to the isocenter in a y-direction, determine a third distance from the center of the phantom to the isocenter in an x-direction, and move the table the first, second, and third distances to align the center of the phantom with the isocenter of the imaging system. In a first example of the method, the method further comprises: determining a rotation to level about a z-axis and rotating the table to level the table. In a second example of the method, optionally including the first example, determining the first distance comprises applying an edge finding algorithm to determine whether the phantom is in view.

As used herein, an element or step recited in the singular and proceeded with the word “a” or “an” should be understood as not excluding plural of said elements or steps, unless such exclusion is explicitly stated. Furthermore, references to “one embodiment” of the present invention are not intended to be interpreted as excluding the existence of additional embodiments that also incorporate the recited features. Moreover, unless explicitly stated to the contrary, embodiments “comprising,” “including,” or “having” an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for an imaging system, comprising:
- acquiring scan data of a phantom;
- determining one or more distances to a center of the imaging system of the phantom, wherein determining the one or more distances to the center of the imaging system of the phantom comprises determining a first amount of lateral misalignment;
- determining a second amount of tilt misalignment; and
- automatically adjusting a position of the phantom based on the first amount of lateral misalignment and the second amount of tilt misalignment.

2. The method of claim 1, wherein determining the first amount of lateral misalignment comprises:
- locating edges of the phantom;
- determining a first distance to center in the z-direction of the one or more distances to center; and
- determining second and third distances to center in an x-direction and a y-direction, respectively, of the one or more distances to center.

3. The method of claim 2, wherein automatically adjusting the position of the phantom based on the one or more distances to the center comprises adjusting a table of the imaging system the first distance to center in the z-direction, the second distance to center in the x-direction, and the third distance to center in the y-direction.

4. The method of claim 2, wherein automatically adjusting the position of the phantom based on the one or more distances to the center comprises adjusting a table of the imaging system the first distance to center in the z-direction and the third distance to center in the y-direction.

5. The method of claim 1, wherein, when the phantom is a step phantom, determining the one or more distances to the center comprises, for each step of the step phantom:
- applying an edge finding algorithm to the scan data;
- determining the first amount of lateral misalignment of the step phantom in x and y directions; and
- determining the second amount of tilt misalignment of the step phantom.

6. The method of claim 1, wherein determining the second amount of tilt misalignment comprises determining a difference between a first pixel count of left-most pixels and a second pixel count of right-most pixels.

7. The method of claim 1, further comprising outputting the one or more distances to center to an operator console.

8. The method of claim 1, wherein the imaging system is one of a photon counting computerized tomography (PCCT) system and a computerized tomography (CT) system.

9. The method of claim 1, wherein the first amount of lateral misalignment comprises a first distance to the center in an x direction and a second distance to the center in a z direction and the second amount of tilt misalignment comprises a rotation to level amount.

10. A system, comprising:
- a computing device communicably coupled to an imaging system configured to image a step phantom, the computing device configured with instructions in non-transitory memory that when executed cause the computing device to:
  - identify the step phantom to be imaged;
  - acquire scan data of the step phantom;
  - determine, for each step of the step phantom, an amount of misalignment of the corresponding step of the step phantom in one or more directions; and
  - automatically adjust a position of the step phantom for the corresponding step based on the amount of misalignment of the corresponding step.

11. The system of claim 10, wherein identifying the step phantom comprises one or more of receiving user input selecting the step phantom from a menu of phantom options and radiofrequency identification tag (RFID) confirmation.

12. The system of claim 10, wherein, to determine the amount of misalignment of the step phantom, the computing device is further configured with instructions stored in non-transitory memory that when executed cause the computing device apply an edge finding algorithm to determine position of edges of the step phantom in a z-direction.

13. The system of claim 10, wherein the scan data is an axial scan of the step phantom and wherein the computing device is further configured with instructions that when executed, cause the computing device to extract scan views at 180 and 90 degrees.

14. The system of claim 13, wherein, to determine the amount of misalignment of the step phantom, the computing device is further configured with instructions stored in non-transitory memory that when executed cause the computing device to:
- finding and extracting the step phantom from each of the scan views at 180 and 90 degrees;
- determining a position of a center of the step phantom in an x-direction and a position of the center of the phantom in the y-direction; and
- comparing the position of the center of the step phantom to an isocenter of the imaging system.

15. The system of claim 10, wherein, to determine the amount of misalignment of the step phantom, the computing device is further configured with instructions stored in non-transitory memory that when executed cause the computing device to:
- determine a first pixel count of left-most pixels of the scan data;
- determine a second pixel count of right-most pixels of the scan data; and
- determine a difference between the first and second pixel counts to determine tilt misalignment of the amount of misalignment.

16. The system of claim 10, wherein the computing device is configured to automatically adjust the position of the step phantom by adjusting a position of a table on which the step phantom is placed in a z-direction and a y-direction via a table motor controller.

17. The system of claim 16, wherein the computing device is additionally configured to automatically adjust the position of the table in an x-direction via the table motor controller.

18. The system of claim 10, wherein, to determine the amount of misalignment of the step phantom, the computing device is further configured with instructions in non-transitory memory that when executed cause the computing device to:

reconstruct a sinogram of a single row of a detector of the imaging system;

track three or more designated points of the step phantom across different angle views of an axial scan;

determine distances between each of the three or more designated points and an isocenter channel of the imaging system for each of the different angle views;

based on the distances between each of the three or more designated points and the isocenter channel and an angle of a gantry of the imaging system, determine locations of each of the three or more designated points; and determine a position of the step phantom relative to an isocenter of the imaging system based on the locations of the three or more designated points.

19. A method for automatically centering a phantom, comprising:

acquiring scan data of the phantom on a table with an imaging system;

determining a first distance from a center of the phantom to an isocenter of the imaging system in a z-direction by applying an edge finding algorithm to determine whether the phantom is in view of the imaging system;

determining a second distance from the center of the phantom to the isocenter in a y-direction;

determining a third distance from the center of the phantom to the isocenter in an x-direction; and moving the table the first, second, and third distances to align the center of the phantom with the isocenter of the imaging system.

20. The method of claim 19, further comprising determining a rotation to level about a z-axis and rotating the table to level the table.

* * * * *